United States Patent
Bao et al.

(10) Patent No.: US 10,113,037 B2
(45) Date of Patent: *Oct. 30, 2018

(54) SILICONE SURFACTANT, W/O EMULSION COMPOSITION, POWDER COMPOSITION, AND COSMETIC/MEDICAL APPLICATION THEREOF

(71) Applicants: DOW CORNING TORAY CO., LTD., Tokyo (JP); Dow Corning (China) Holding Co., Ltd., Shanghai (CN)

(72) Inventors: Xinyan Bao, Shanghai (CN); Seiji Hori, Fukui (JP); Sayuri Kikunaga, Chiba (JP); Yang Wang, Shanghai (CN)

(73) Assignees: DOW CORNING TORAY CO., LTD., Tokyo (JP); DOW (SHANGHAI) HOLDING CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/300,899

(22) PCT Filed: Apr. 3, 2014

(86) PCT No.: PCT/CN2014/074712
§ 371 (c)(1),
(2) Date: Sep. 30, 2016

(87) PCT Pub. No.: WO2015/149322
PCT Pub. Date: Oct. 8, 2015

(65) Prior Publication Data
US 2017/0022327 A1    Jan. 26, 2017

(51) Int. Cl.
| | | |
|---|---|---|
| *C08G 77/46* | (2006.01) |
| *C08L 83/12* | (2006.01) |
| *A61K 8/895* | (2006.01) |
| *A61Q 1/10* | (2006.01) |
| *A61Q 1/06* | (2006.01) |
| *A61Q 1/00* | (2006.01) |
| *A61Q 5/02* | (2006.01) |
| *A61Q 19/08* | (2006.01) |
| *A61Q 15/00* | (2006.01) |
| *A61Q 19/10* | (2006.01) |
| *A61Q 19/00* | (2006.01) |
| *A61Q 5/12* | (2006.01) |

(52) U.S. Cl.
CPC .............. *C08G 77/46* (2013.01); *A61K 8/895* (2013.01); *A61Q 1/00* (2013.01); *A61Q 1/06* (2013.01); *A61Q 1/10* (2013.01); *A61Q 5/02* (2013.01); *A61Q 5/12* (2013.01); *A61Q 15/00* (2013.01); *A61Q 19/007* (2013.01); *A61Q 19/08* (2013.01); *A61Q 19/10* (2013.01); *C08L 83/12* (2013.01)

(58) Field of Classification Search
CPC ......... C08G 77/46; C08L 83/12; A61K 8/895; A61Q 19/08; A61Q 19/007; A61Q 15/00; A61Q 5/12; A61Q 19/10; A61Q 1/10; A61Q 1/06; A61Q 1/00; A61Q 5/02
See application file for complete search history.

(56) References Cited

U.S. PATENT DOCUMENTS

| | | | |
|---|---|---|---|
| 4,698,178 A | 10/1987 | Huttinger et al. | |
| 7,279,503 B1 | 10/2007 | O'Lenick, Jr. | |
| 9,744,118 B2 * | 8/2017 | Hayashi ................. A61K 8/894 |
| 2003/0158363 A1 | 8/2003 | Nakanishi | |
| 2003/0185771 A1 | 10/2003 | Kamei et al. | |
| 2005/0008592 A1 * | 1/2005 | Gardel ..................... A61K 8/06 |
| | | | 424/63 |
| 2007/0275618 A1 | 11/2007 | Lorentz et al. | |
| 2010/0105843 A1 | 4/2010 | Knott et al. | |
| 2011/0182846 A1 | 7/2011 | Ikeda et al. | |
| 2012/0251605 A1 | 10/2012 | Iimura et al. | |
| 2012/0263662 A1 | 10/2012 | Iimura et al. | |

(Continued)

FOREIGN PATENT DOCUMENTS

| | | |
|---|---|---|
| CN | 101891894 B | 7/2013 |
| EP | 1123697 A1 | 8/2001 |

(Continued)

OTHER PUBLICATIONS

PCT/CN2014/074712 International Search Report dated Jan. 8, 2015, 3 pages.
English language abstract and machine translation for JPH0753326 (A) extracted from http://worldwide.espacenet.com database on Sep. 14, 2016, 14 pages.
English language abstract and machine translation for JP2719303 (A) extracted from http://worldwide.espacenet.com database on Aug. 14, 2016, 22 pages.
English language abstract and machine translation for JPH10167946 (A) extracted from http://worldwide.espacenet.com database on Aug. 14, 2016,15 pages.
English language abstract and machine translation for JP2009184975 (A) extracted from http://worldwide.espacenet.con database on Jun. 25, 2018, 23 pages.

*Primary Examiner* — Blessing M Fubara
(74) *Attorney, Agent, or Firm* — Warner Norcross & Judd LLP

(57) ABSTRACT

A novel silicone surfactant comprises a co-modified organopolysiloxane copolymer having a long chain alkyl group, a polyether group, and a specific average polymerization degree of its siloxane back-bone. The silicone surfactant can be used for an emulsifier (especially for a water-in-oil (W/O) type emulsifier), a surface treatment agent, a powder treatment agent, or a dispersant in a cosmetic composition or a medicament. A W/O emulsion composition comprising the silicone surfactant; a powder composition where the surface of the powder is treated using the silicone surfactant as a powder treatment agent; a powder composition further comprising an oil agent and having a form of powder in oil dispersion; and a preparation for external use, particularly a cosmetic composition or medicament, comprising the same; are also disclosed.

16 Claims, No Drawings

(56) References Cited

U.S. PATENT DOCUMENTS

| | | |
|---|---|---|
| 2012/0269747 A1 | 10/2012 | Iimura et al. |
| 2012/0269875 A1 | 10/2012 | Tamura et al. |
| 2013/0102686 A1 | 4/2013 | Tamura et al. |
| 2013/0210930 A1 | 8/2013 | Souda et al. |
| 2014/0004065 A1 | 1/2014 | Souda et al. |
| 2014/0323590 A1 | 10/2014 | Iimura et al. |
| 2014/0371330 A1 | 12/2014 | Hayashi et al. |
| 2015/0272858 A1* | 10/2015 | Hayashi .................. A61Q 1/02 424/401 |

FOREIGN PATENT DOCUMENTS

| | | |
|---|---|---|
| EP | 2103301 A1 | 9/2009 |
| EP | 2905319 A1 | 8/2015 |
| JP | S6190732 A | 5/1986 |
| JP | H0753326 A | 2/1995 |
| JP | 2719303 B2 | 11/1997 |
| JP | H10167946 A | 6/1998 |
| JP | 200238013 A | 2/2002 |
| JP | 2009184975 A | 8/2009 |
| JP | 2011148784 A | 8/2011 |
| JP | 2011149017 A | 8/2011 |
| JP | 2011246704 A | 12/2011 |
| JP | 2011246705 A | 12/2011 |
| JP | 2011246706 A | 12/2011 |
| JP | 2012149052 A | 8/2012 |
| JP | 2013151657 A | 8/2013 |
| WO | WO2007109240 A2 | 9/2007 |
| WO | WO2009006091 A2 | 1/2009 |
| WO | WO2009022621 A1 | 2/2009 |
| WO | WO2011028765 A1 | 3/2011 |
| WO | WO2011028770 A1 | 3/2011 |
| WO | WO2011049246 A1 | 4/2011 |
| WO | WO2011049248 A1 | 4/2011 |
| WO | WO2011136394 A1 | 11/2011 |
| WO | WO 2014/054693 * | 10/2014 |

* cited by examiner

SILICONE SURFACTANT, W/O EMULSION COMPOSITION, POWDER COMPOSITION, AND COSMETIC/MEDICAL APPLICATION THEREOF

CROSS-REFERENCE TO RELATED APPLICATIONS

This application claims priority to, all advantages of, and is the National Stage of International Application No. PCT/CN2014/074712 filed on 3 Apr. 2014, the content of which is hereby incorporated by reference.

TECHNICAL FIELD

The present invention relates to a novel silicone surfactant comprising co-modified organopolysiloxane copolymer having a long chain alkyl group and a polyether group in the molecule and specific average polymerization degree of siloxane backbone; and a use of the silicone surfactant for an emulsifier (especially W/O type emulsifier), a surface treatment agent, a powder treatment agent, or a dispersant in cosmetic composition or medicament. Furthermore, the present invention relates to a water in oil (W/O) emulsion composition comprising said silicone surfactant, a powder composition where the surface of the powder is treated using said silicone surfactant as a powder treatment agent, a powder composition further comprising oil agent and having a form of powder in oil dispersion; and, moreover a preparation for external use, particularly a cosmetic composition or medicament, comprising the same. Additionally, this invention also provides a convenient production method of transparent W/O emulsion.

BACKGROUND ART

Various powders exemplified by white and colored pigments such as titanium oxide, zinc oxide, red iron oxide, and the like and extender pigments such as mica, sericite, and the like are widely used in the fields of base cosmetic compositions and other various cosmetic compositions such as sunscreens, nail colors, nail coats, foundations, mascaras, eye liners, and the like. However, untreated powder is prone to agglomerate due to the electric charge and polarity, trace amounts of impurities, and the like on the powder surface. Therefore, powders that have been subject to various surface treatments are widely used for the purpose of enhancing dispersibility and stability of a powder in a cosmetic composition and also improving the tactile sensation, moisture resistance, sebum resistance, and the like of a cosmetic composition comprising a powder.

Known examples of such surface treatments include lipophilization treatments using an oil agent, a metal soap, or the like; hydrophilization treatments using a surfactant, a water-soluble polymer, or the like; hydrophobization treatments using silicone compounds; silica treatments; alumina treatments; and the like. Particularly, in recent years, there have been many cases where a surface treatment using a silicone compound having a reactive moiety in the molecule has been performed. The reactive moiety forms a chemical bond with the powder surface and, as a result, the surface treatment using the silicone compound is effective from the perspective of simultaneously modifying the surface of the powder and blocking the surface activity of the powder without significantly altering the characteristics of the powder itself. Additionally, because surface treatment can be thoroughly performed, the treatment agent will not separate from the powder surface, even when compounded in a cosmetic composition comprising a solvent. An example of such a surface treatment is a method in which a powder is surface treated using a methylhydrogenpolysiloxane (Patent Document 1). However, in this method, unreacted Si—H groups still remain even after the surface treating of the powder and, therefore, there is a problem when this powder is compounded in a cosmetic composition because hydrogen gas may be produced depending on the components and the like in the cosmetic composition.

On the other hand, methods for manufacturing a powder dispersion using a hydrophilic modified organopolysiloxane that has good compatibility with the powder surface have been proposed. Examples thereof include a method for forming a polyether-modified organopolysiloxane into a powder dispersing aid (Patent Document 2) and a method for forming an organopolysiloxane modified by polyglycerine or a similar polyhydric alcohol into a powder dispersing aid (Patent Document 3). However, there are problems in that the powder dispersion effectiveness is still insufficient, viscosity of a power dispersion obtained by dispersing a powder in silicone oil or a similar oil agent increases gradually over time, fluidity is lost, and the like.

As a method to solve the problems described above, the present applicant has proposed methods using a co-modified organopolysiloxane copolymer having a group that has a carbosiloxy dendron structure and a glycerin derivative, polyhydric alcohol, or similar hydrophilic group in the molecule (Patent Documents 4, 5, and 6). Such co-modified organopolysiloxanes are safe and do not produce hydrogen, and can be advantageously used in the surface treating of a powder. Moreover, affinity with other raw materials of cosmetic compositions is superior, and the dispersibility and stability of the powder in a cosmetic composition comprising a powder can be enhanced.

Generally, in some instances, formulations principally comprising silicone as an oil agent tend to have excessively light tactile sensation due to the characteristics of the silicone. However, to meet a broad range of consumer needs, cosmetic compositions having different tactile sensations need to be prepared and, particularly, in order to provide a feeling of luxury, formulations that deliver a tactile sensation with weight are preferable. Additionally, regarding the preparation of such systems, the development of formulations comprising oil agents other than silicone (e.g. isododecane, various hydrocarbon solvents, and the like) has also been actively investigated. However, with the co-modified organopolysiloxane described above, there has been a problem in that the desired dispersibility in the hydrocarbon solvent cannot be achieved because molecular design is carried out with silicone-based formulations principally in mind. Thus, there is a pressing need for the development of a dispersing agent and a silicone-based activating agent that is soluble in a hydrocarbon solvent.

Patent Document 7 describes an alkyl-modified silicone polyether that is also cost-efficient as a solution to the problems described above. This co-modified organopolysiloxane copolymer is mainly used as an emulsifier but is also used as a dispersing agent and is applied to various types of powder cosmetic compositions. However, these copolymers all have comparatively high molecular weights and a large number of hydrophilic groups, leading to the problem of dispersibility in microparticulate powders being poor or the problem of stickiness occurring when added to the formulation. On the other hand, in the case that the molecular weight is too small, it will become hard to work as an emulsifier and keep an emulsion composition stable. Therefore, these documents substantially fail to disclose or suggest a silicone surfactant having both emulsification capability for emulsifiers and surface treating capability for powder-dispersant.

PRIOR ART DOCUMENTS

Patent Documents

Patent Document 1: Japanese Unexamined Patent Application Publication No. H07-053326A (Japanese Patent No. 2719303)
Patent Document 2: Japanese Unexamined Patent Application Publication No. H10-167946A
Patent Document 3: Japanese Unexamined Patent Application Publication No. 2002-038013A
Patent Document 4: WO2011/049246
Patent Document 5: WO2011/049248
Patent Document 6: WO2011/136394
Patent Document 7: Japanese Unexamined Patent Application Publication No. S61-090732A

SUMMARY OF INVENTION

Technical Problem

A first object of the present invention is to provide a novel silicone surfactant of co-modified organopolysiloxane by which the problems described above are solved. More specifically, a first object of the present invention is to provide a silicone surfactant that can be advantageously used as a cosmetic composition raw material which, compared to conventional co-modified silicones, has both excellent emulsification capability and powder dispersibilty with superior compatibility with a wide range of hydrocarbon solvents. A second object of the present invention is to provide a silicone surfactant having superior functions as an emulsifier (especially W/O type emulsifier), a surface treatment agent, a powder treatment agent, or a dispersant in cosmetic composition or medicament. A third object of the present invention is to provide a water in oil emulsion composition comprising said silicone surfactant, a powder composition wherein the surface of the powder is treated using said silicone surfactant as a powder treatment agent, a powder composition further comprising oil agent and having a form of powder in oil dispersion; and, moreover a preparation for external use, particularly a cosmetic composition or medicament, comprising the same.

Solution to Problem

As a result of intensive investigation aimed at achieving the above objects, the present inventors arrived at the present invention. Specifically, the first object of the present invention is achieved by novel silicone surfactant comprising a co-modified organopolysiloxane having both long-alkyl group and polyether group in a molecule, and further having specific average polymerization degree of siloxane backbone for each siloxane units. Note that in the present invention, the term "average polymerization degree of siloxane backbone" refers to the average polymer structure that is calculated by $^{29}$Si NMR.

Additionally, the second object of the present invention is achieved by a use of said silicone surfactant for an emulsifier, a surface treatment agent, powder treatment agent, or a dispersant in cosmetic composition or medicament. Furthermore, the third object of the present invention is achieved by a water in oil emulsion composition comprising said silicone surfactant, a powder composition wherein the surface of the powder is treated using said silicone surfactant as a powder treatment agent, a powder composition further comprising oil agent and having a form of powder in oil dispersion; and, moreover a preparation for external use, particularly a cosmetic composition or medicament, comprising the same.

Specifically, the objects of the present invention are achieved by:

[1] A silicone surfactant comprising a co-modified organopolysiloxane represented by the following general formula (1):

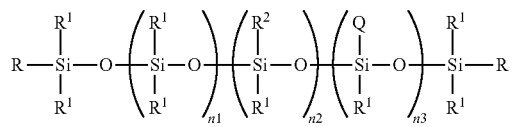

wherein, in the general formula (1),
$R^1$ is a monovalent hydrocarbon group having from 1 to 30 carbons, or a hydrogen atom;
$R^2$ is a s straight or branched monovalent hydrocarbon group having from 6 to 30 carbons; and Q is a hydrophilic group consisting of a polyoxyalkylene group represented by structural formula (2) below:

$$-(C_2H_4O)_r-(C_3H_6O)_s-R^3 \qquad (2)$$

wherein, $R^3$ is a hydrogen atom or an alkyl group having from 1 to 4 carbons, r is a number in a range of 0 to 100, s is a number in a range of 0 to 50, and r+s is a number in a range of 3 to 100; R is a group selected from $R^1$, $R^2$, and Q; provided that, when n3=0, at least one R is Q; (n1+n2+n3) is a number in a range of 40 to 75; n1 is a number in a range of 1 to 65; n2 is a number in a range of 1 to 20; and n3 is a number in a range of 0 to 5.

[2] The silicone surfactant of [1], wherein the co-modified organopolysiloxane is represented by following structural formula (1-1):

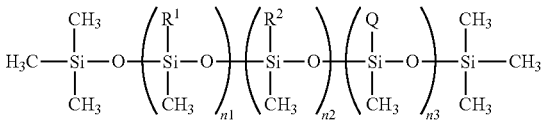

wherein, $R^1$, $R^2$, and Q are groups synonymous with the groups described above, (n1+n2+n3) is a number in a range of 40 to 75, n1 is a number in a range of 2 to 55, n2 is a number in a range of 3 to 20, and n3 is a number in a range of 0.5 to 5.

[3] The silicone surfactant of [1] or [2], having more than 30 wt % of content of hydrocarbon group of $R^2$ having from 6 to 30 carbons, which is calculated by weight ratio of $R^2$ group content to total molecular weight of the co-modified organopolysiloxane represented by said structural formula (1) or (1-1).

[4] A use of the silicone surfactant according to any of [1] to [3] for at least one ingredient selected from the group consisting of an emulsifier, a surface treatment agent, powder treatment agent, or a dispersant in cosmetic composition or medicament.

[5] A water in oil (W/O) emulsion composition comprising: (A) the silicone surfactant described in any of [1] to [3], (B) water, and (C) at least one oil agent.

[6] A powder composition comprising: (A) the silicone surfactant described in any of [1] to [3]; and (D) a powder or coloring agent.

[7] The powder composition according to [6], wherein the component (D) is one or two or more selected from the group consisting of an inorganic pigment powder, an organic pigment powder, and a resin powder, having an average diameter in a range of 1 nm to 20 μm.

[8] The powder composition according to [6] or [7], further comprising (C) at least one oil agent.

[9] A preparation for external use comprising the silicone surfactant of any of [1] to [3].

[10] The preparation for external use according to [9] that is a cosmetic composition or a medicament.

[11] A cosmetic composition or a medicament comprising the water in oil (W/O) emulsion composition of [5].

[12] A cosmetic composition or a medicament comprising the powder composition of any of [6] to [8].

[13] A cosmetic composition or a medicament comprising the silicone surfactant of any of [1] to [3], wherein the cosmetic composition or medicament is in substantially water-free form.

[14] A method of adjusting transparency of the water in oil (W/O) emulsion composition of [5] comprising following steps:

step (i) of independently mixing an aqueous phase including the component (B) and an oil phase including the component (A) and the component (C), step (ii) of adjusting a difference between refractive indexes at 25° C. of both phases so as to be less than or equal to 0.0020 units, and step (iii) of emulsifying the water phase into the oil phase.

Advantageous Effects of Invention

According to the present invention, said silicone surfactant of co-modified organopolysiloxane that can be advantageously used as a cosmetic/medical raw material, especially for an emulsifier, a surface treatment agent, powder treatment agent, or a dispersant in cosmetic composition or medicament. The silicone surfactant is characterized by having both functions of excellent emulsification effect and of powder dispersibilty with superior compatibility with a wide range of hydrocarbon solvents. Especially, when the silicone surfactant is applied for a W/O type emulsifier in the cosmetic or medical composition, the viscosity of obtained emulsion can be relatively low and the emulsion itself keeps excellent temporal stabilities. As a result, preparation of particularly a water in oil emulsion or a powder in oil dispersion is facilitated and, moreover, the obtained emulsion product is characterized by having stable emulsification state with low viscosity. Furthermore, by using said silicone surfactant, the transparency of the emulsion is adjusted in relatively convenient method of production.

Additionally, according to the present invention, an emulsifier with capability of powder treatment agent comprising the organopolysiloxane, a powder that is surface treated using the powder treatment agent, a water in oil emulsion composition or a powder composition comprising the co-modified organopolysiloxane copolymer, and a powder in oil dispersion comprising an oil agent; and, moreover a preparation for external use, particularly a make-up cosmetic composition can be provided. A variety of cosmetic compositions comprising the novel co-modified organopolysiloxane of the present invention can be provided.

DESCRIPTION OF EMBODIMENTS

Hereinafter, a novel silicone surfactant of the present invention, uses thereof as various types of emulsifier or treatment agents, particularly uses as a water in oil emulsifier with capability of powder treatment agent and as a cosmetic raw material are described in detail. Additionally, detailed descriptions of a water in oil emulsion or powder in oil dispersion, a preparation for external use, advantageously a cosmetic/medical composition, and particularly advantageously a make-up cosmetic composition, using the novel silicone surfactant comprising co-modified organopolysiloxane of the present invention will be given.

The co-modified organopolysiloxane according to the present invention has a long chain alkyl group and a polyoxyalkylene group in the molecule, and has an average polymerization degree of siloxane backbone is 40 to 75. Specifically the co-modified organopolysiloxane is represented by general formula (1) below.

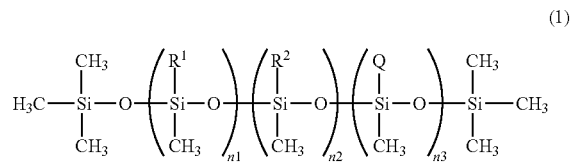

In general formula (1),
$R^1$ is a monovalent hydrocarbon group having from 1 to 30 carbons, or a hydrogen atom.
$R^2$ is a straight or branched monovalent hydrocarbon group having from 6 to 30 carbons; and Q is a hydrophilic group consisting of a polyoxyalkylene group represented by structural formula (2) below.

General Formula (2):

$$—(C_2H_4O)_r—(C_3H_6O)_s—R^3 \quad (2)$$

In this formula, $R^3$ is a hydrogen atom or an alkyl group having from 1 to 4 carbons, r is a number in a range of 0 to 100, s is a number in a range of 0 to 50, and r+s is a number in a range of 3 to 100.

R is a group selected from $R^1$, $R^2$, and Q; provided that, when n3=0, at least one R is Q; (n1+n2+n3) is a number in a range of 40 to 75; n1 is a number in a range of 1 to 30; n2 is a number in a range of 1 to 20; and n3 is a number in a range of 0 to 5.

Average polymerization degree of siloxane backbone, (n1+n2+n3) calculated by 29Si NMR, is from 40 to 75. If the average polymerization degree of the siloxane backbone exceeds the upper limit described above, functionality, namely emulsifying property and powder dispersibility will be insufficient. More specifically, if the average polymerization degree of the siloxane backbone exceeds the upper limit described above, the viscosity of an obtained emulsion composition or an obtained powder dispersion (particularly a slurry powder in oil dispersion) will be high and/or dispersion of the powder will impair the advantage as provided by the current invention, thus leading to difficulty when using the co-modified organopolysiloxane as a cosmetic raw material. Moreover, depending on the preparation conditions, in some cases, it may be impossible to fabricate a powder dispersion. In addition to that, if the average polymerization degree of the siloxane backbone is smaller than the lower limit described above, it will become hard to control dispersibility since the performance of the co-modified organopolysiloxane can be affected by odor attenuating treatment. For cosmetic applications, low odor is greatly required but when odor attenuating treatment is applied using material such as acidic substance, that affects chemical structure of impurities in the co-modified organopolysiloxane and if the average polymerization degree of the siloxane backbone is smaller than the lower limit described above, dispersibility can be strongly affected by the treatment. Average polymerization degree of the siloxane backbone from 40 to 75 can provide the best balance of dispersibility and emulsification capability offering low odor feature. In addition, when the co-modified organopolysiloxane has more than 30 wt % of alkyl content, dispersibility is further improved and that can inhibit viscosity increase of composition, especially powder composition.

In general formula (1), $R^1$ is a monovalent hydrocarbon group having from 1 to 30 carbons, or a hydrogen atom. However, the monovalent organic group $R^1$ particularly independently represents an aryl group or an alkyl group having from 1 to 10 carbons. Examples thereof include methyl, ethyl, n-propyl, i-propyl, n-butyl, i-butyl, s-butyl, pentyl, neopentyl, cyclopentyl, hexyl, and similar straight, branched, or annular alkyl groups; and phenyl groups. From a technical point of view, $R^1$ preferably is a methyl group or a phenyl group. Additionally, $R^1$ may be a group wherein the hydrogen atoms bonded to the carbon atoms of these groups are substituted at least partially by fluorine or a similar halogen atom, or by an organic group having an epoxy group, an acyl group, a carboxyl group, an amino group, a (meth)acryl group, a mercapto group, or the like.

$R^2$ is a straight or branched monovalent hydrocarbon group having from 6 to 30 carbons. Particularly, in cases where all of the $R^1$ moieties are alkyl groups having not more than 5 carbons (particularly methyl groups) or are phenyl groups, it is preferable that the long chain hydrocarbon group $R^2$ be comprised for the purpose of improving affinity with, particularly, hydrocarbon-based oil agents (i.e. cosmetic raw materials). Preferable examples of the $R^2$ moiety include hexyl groups, heptyl groups, octyl groups, decyl groups, dodecyl groups, hexadecyl groups, and similar alkyl groups having not less than 6 carbons; cyclohexyl groups and similar cycloalkyl groups; tolyl groups, xylyl groups, naphthyl groups, and similar aryl groups; and groups wherein the hydrogen atoms bonded to the carbon atoms of these groups are substituted at least partially by fluorine or a similar halogen atom, or an organic group having an epoxy group, an acyl group, a carboxyl group, an amino group, a (meth)acryl group, a mercapto group, or the like. The $R^2$ moiety is preferably an alkyl group having from 8 to 20 carbons and more preferably an alkyl group having from 12 to 20 carbons. From a viewpoint of emulsion stability and powder dispersibility in lower viscosity of obtained slurry by the co-modified organopolysiloxane of this invention, the content of hydrocarbon group of $R^2$ having from 6 to 30 carbons is preferred to be more than 30 wt % of total molecular weight of the co-modified organopolysiloxane. More specifically, the content of hydrocarbon group of $R^2$ having from 6 to 30 carbons is calculated by weight ratio of $R^2$ group to total molecular weight of the co-modified organopolysiloxane represented by said structural formula (1) or (1-1). More preferably, the $R^2$ moiety is an alkyl group having from 8 to 20 carbons and the content of $R^2$ moiety is in a range of from 30 to 40 wt %, most preferably, from 30 to 35 wt %. When the content of hydrocarbon group of $R^2$ is in said range, the silicone surfactant of this invention perform both functions of excellent emulsification effect to almost all type of oil agents and of powder dispersibility In general formula (1), Q is defined as a polyoxyalkylene group represented by general formula (2) shown above. Q is a moiety that imparts hydrophilicity to the co-modified organopolysiloxane according to the present invention and, for example, may be a group with a branched structure such as a branched polyoxyalkylene group.

In general formula (2), $R^3$ is a hydrogen atom or an alkyl group having from 1 to 4 carbons, and preferably is a hydrogen atom.

r is a number in a range of 0 to 100 and s is a number in a range of 0 to 50.

Preferably, r is a number in a range of 1 to 50 and s is a number in a range of 0 to 40.

More preferably, r is a number in a range of 2 to 40 and s is a number in a range of 0 to 30.

Even more preferably, r is a number in a range of 3 to 30 and s is a number in a range of 0 to 20.

Additionally, r+s is a number in a range of 3 to 100, preferably a number in a range of 6 to 50, and more preferably a number in a range of 8 to 40.

In general formula (1), (n1+n2+n3) is a number in a range of 40 to 75. n1 is a number in a range of 1 to 65, preferably from 2 to 55, and more preferably from 3 to 45. n2 is a number in a range of 1 to 20, preferably from 2 to 20, and more preferably from 3 to 20. n3 is a number in a range of 0 to 5, preferably from 0.5 to 5, and more preferably from 1.0 to 4.

Industrially preferable examples of the co-modified organopolysiloxane according to the present application include a straight co-modified organomethylpolysiloxane represented by structural formula (1-1-1) below.

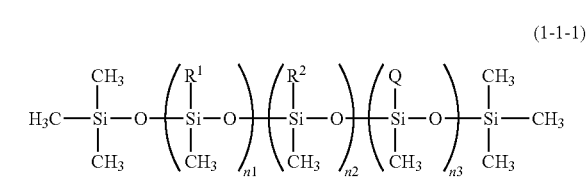

(1-1-1)

In this formula, $R^1$, $R^2$, and Q are groups synonymous with the groups described above, and n1 to n3 are numbers synonymous with the numbers described above.

The co-modified organopolysiloxane according to the present application described above can be obtained by addition-reacting a polyoxyalkylene compound, which has an alkenyl group or similar reactive functional group, and a long chain alkyl compound having one carbon-carbon double bond at one end of the molecular chain, with an organopolysiloxane that has a Si—H or similar reactive functional group. The type of addition reaction is not particularly limited but, from the standpoint of reaction control, purity, and yield, the addition reaction is preferably performed in the presence of a hydrosilylation reaction catalyst. Additionally, a crude co-modified organopolysiloxane product obtained via the addition reaction may be refined by performing a deodorizing treatment by hydrogenation reaction in the presence of a hydrogenation catalyst in a solvent or without a solvent; or may be subjected to an odor attenuating treatment using an acidic substance. Furthermore, the co-modified organopolysiloxane may be a mixture with a polyoxyalkylene compound having an alkenyl group or similar reactive functional group.

With regards to the synthesis of the co-modified organopolysiloxane according to the present application, the same method recited in paragraphs 0110 to 0122 of Patent Document 5 (WO2011/049248, filed by the present applicant), specifically, reacting, refining, and odor attenuating treating or the like using an acidic substance, can be used.

Uses of Silicone Surfactant

The silicone surfactant comprising said co-modified organopolysiloxane according to the present invention (hereinafter referred to as "component (A)") is hydrophobic, has both a long chain alkyl group and a hydrophilic polyoxyalkylene group in the same molecule, and also has a specific polymerization degree of siloxane-backbone. As a result, the co-modified organopolysiloxane can be used as silicone surfactant having both functionalities of water in oil emulsifier and surface treatment agent. Especially, the novel silicone surfactant is useful for at least one ingredient selected from the group consisting of an emulsifier, a surface treatment agent, powder treatment agent, or a dispersant in cosmetic composition or medicament. Furthermore, the co-modified organopolysiloxane according to the present invention is extremely useful as a water in oil emulsifier and a powder treatment agent used in the surface treating of powder and the dispersion of powder.

The Use of the Silicone Surfactant for an Emulsifier

The silicone surfactant of the present invention exhibits particularly excellent emulsification performance when used alone, and can therefore finely and stably emulsify/disperse an aqueous phase, powder or the like not only in cases where the oil phase is a silicone oil, ester oil or triglyceride, but also in cases where the oil phase is primarily a non-polar organic oil such as a mineral oil and isododecane, which was difficult with conventional polyether-modified silicones, and can therefore produce a composition having excellent stability over time or when subjected to heat. In particular, the silicone surfactant of the present invention can contain a long chain alkyl group, can arbitrarily contain a silylalkyl group having a siloxane dendron structure that is hydrophobic and exhibits high water repellency, and/or a chain polysiloxane group, and can have these and a hydrophilic group within the same molecule. Therefore, the silicone surfactant of the present invention is extremely useful as a surfactant or dispersing agent that can produce a stable composition having an oil agent as the continuous phase in a wide variety of oil agent systems (a water-in-oil emulsion composition, a polyol-in-oil type emulsion composition, a polar solvent-in-oil type emulsion composition or a powder-in-oil dispersion). The silicone surfactant of the present invention is particularly preferable as an emulsifier for a water-in-oil emulsion.

In addition, the silicone surfactant of the present invention can stabilize a wide variety of oil agent-containing emulsion systems in a variety of oil agent-containing W/O emulsion formulations without being aided by an oil gelling agent such as an organic emulsifier, and a clay mineral that has been hydrophobized/oil-swelled by means of a quaternary ammonium salt-based organic cation or the like, and can therefore maximize the synergistic effect in terms of feeling to touch of an oil agent and the silicone surfactant and provide a W/O emulsion type external use preparation or cosmetic composition having a soft and natural feeling to touch, light smoothness, good spreadability and excellent moisture retention.

In addition, use of the novel silicone surfactant according to the present invention and/or a composition containing the same as a surfactant is the same as the use of the co-modified organopolysiloxane disclosed by the applicants in paragraphs [0124] to [0147] of the aforementioned Patent Document 5 (WO 2011/049248) as a surfactant and the preparation of a variety of emulsion composition, and the silicone surfactant according to the present invention is particularly suitable as a surfactant used in a water-in-oil emulsion cosmetic composition.

<Dispersing Agent and Emulsifier for Water-in-Oil Emulsion>

The silicone surfactant of the present invention can be used as an emulsifier or a dispersing agent that can produce a stable composition having an oil agent as the continuous phase (a water-in-oil emulsion composition, a polyol-in-oil type emulsion composition, a polar solvent-in-oil type emulsion composition or a powder-in-oil dispersion). In particular, the emulsifier for a water-in-oil emulsion can be advantageously used not only as an emulsifier for an ordinary water-in-oil emulsion in which an aqueous phase is dispersed in an oil phase, but also as an emulsifier for a polyol-in-oil type emulsion in which a polyol phase is dispersed in an oil phase or as an emulsifier for a polar solvent-in-oil type emulsion in which a polar solvent is dispersed in a non-polar oil phase. Furthermore, the silicone surfactant of the present invention exhibits excellent performance as a dispersing agent that uniformly disperses a variety of powders in an oil phase, and can therefore also be used as a powder dispersing agent when preparing a water-in-oil emulsion.

A dispersing agent and emulsifier for a water-in-oil emulsion that contains the silicone surfactant of the present invention is suitable for use in a cosmetic composition or external use preparation, and can be preferably blended as a raw material for a variety of cosmetic compositions and external use preparations. In particular, it is preferable to use the silicone surfactant at a quantity of approximately 0.1 to 40 wt. % relative to the total weight of a cosmetic composition or external use preparation.

Use as a Powder Treatment Agent

The silicone surfactant according to the present invention has specific molecular range and can be oriented on the surface of various powders so as to impart an appropriate degree of water repellency. Therefore, the silicone surfactant according to the present invention can be used for surface treating and dispersing powders for use in cosmetic compositions, and can be advantageously used as a powder surface treatment agent. Particularly, when used as a powder treatment agent, dispersion stability in a hydrocarbon solvent system of the silicone surfactant according to the present invention is superior compared to conventional co-modified organopolysiloxanes. Thus, a powder in oil dispersion having superior stability in which the powder does not agglomerate or precipitate after preparing a powder composition obtained by treating the powder surface using a treatment agent can be provided, even when a method is used where the powder composition is dispersed in an oil agent dispersing medium and even when the powder is one where conventional powder treatment agents result in difficulties in stable dispersion.

The silicone surfactant of the present invention has excellent compatibility with various other hydrophilic and hydrophobic components in the cosmetic composition, and can enhance the dispersibility and stability of a powder in a cosmetic composition that comprises a powder. Thus, the powder treatment agent of the present invention and the powder surface treatment agent of the present invention can improve the stability of a cosmetic composition that comprises a powder and can improve the uniform dispersibility of said powder. A cosmetic composition that comprises a powder that is surface treated using the powder surface treatment agent has high stability and said powder uniformly disperses in said cosmetic composition.

A compounded amount of the silicone surfactant in the powder treatment agent of the present invention is not particularly limited provided that powder treatment effects are displayed and, for example, can be from 50 to 100 wt. % (mass %), and is preferably from 70 to 100 wt. %, and more preferably from 90 to 100 wt. %.

The powder treatment agent of the present invention may comprise a combination of the silicone surfactant according to the present invention and another known surface treatment agent and be used to surface treat a powder. Examples of the other surface treatment agent include surface treatment agents based on methylhydrogenpolysiloxane, silicone resin, metal soap, silane coupling agents, silica, alumina, titanium oxide, and similar inorganic oxides; perfluoroalkylsilane, perfluoroalkyl phosphate ester salts, and similar fluorine compounds. Thus, the powder surface treatment agent of the present invention may, for example, comprise from 0.1 to 50 wt. % of the other surface treatment agent and preferably comprises from 1 to 30 wt. % and more preferably comprises from 5 to 10 wt. % of the other surface treatment agent.

When using the silicone surfactant according to the present invention as the powder surface treatment agent, a compounded amount of the silicone surfactant with the powder or coloring agent is preferably in a range of 0.1 to 30 parts by mass, more preferably 0.5 to 20 parts by mass, and more preferably 1.5 to 15 parts by mass per 100 parts by mass of the powder or coloring agent. If the compounded amount is less than the lower limit described above, effects by the surface treating may be insufficient. On the other hand, even if the compounded amount exceeds the upper limit described above, greater prominent changes in texture will not occur, and the tendency for the powder and the silicone surfactant to form a uniform mixture will increase.

The silicone surfactant according to the present invention can be used to treat a powder surface using a conventional method. This method is not particularly limited and, for example, can be appropriately selected from the methods described below.

1. A method in which the target powder is surface treated by being dispersed in a medium selected from organic solvents in which the treatment agent has been compounded.
2. A method in which the powder is surface treated by mixing the powder and the powder treatment agent and, thereafter, crushing the mixture in a pulverizer such as a ball mill, a jet mill, or the like.
3. A treatment method in which the treatment agent is compounded in a solvent, the powder is dispersed in the mixture so as to adhere the treatment agent to the surface of the powder, and then the powder is dried and sintered.

Powder Composition

Additionally, the present invention relates to a powder composition comprising (A) the silicone surfactant according to the present invention and (B) a powder or coloring agent. The powder composition can be obtained, according to the methods described above or the like, by mixing (B) the powder or coloring agent and (A) the silicone surfactant according to the present invention, regardless of the purpose (i.e. to surface treat the powder, improve dispersibility of the powder, to act as a premix for a cosmetic raw material, or the like).

Powder in Oil Dispersion

Additionally, "powder in oil dispersion" as used in the present invention, refers to a product in which a powder composition obtained as described above is dispersed in an oil agent or, alternatively, a product in which a silicone surfactant is dissolved or dispersed in an oil agent, and then the powder is added by being mixed and dispersed therein; and a form thereof is that of a liquid dispersed product. This liquid dispersed product is also called as "slurry". Particularly, the silicone surfactant according to the present invention is useful on the point that a low viscosity slurry can be prepared under the same conditions as the silicone surfactant recited in Patent Document 5 above, even when the powder is a powder that cannot be sufficiently treated such as zinc oxide or a similar inorganic powder. Additionally, the silicone surfactant according to the present invention has a comparatively low molecular weight and, compared to conventionally known polyether-modified silicones, has superior compatibility and affinity with hydrocarbon oil agents such as isododecane and isohexadecane. As a result, there is a benefit in that powder in oil dispersions having superior dispersion stability, stability over time, and compounding stability can be prepared using a broad range of various cosmetic composition use oil agents, the preparation of which has been conventionally problematic.

The oil agent is not particularly limited provided that a liquid dispersion can be prepared, and is an oil agent that is commonly used as a component of a cosmetic composition. Furthermore, while the oil agent is typically liquid at room temperature, it may by solid such as a wax, and may also be in a highly viscous (high viscosity) gum-like state or paste-like state. The oil agent is preferably one or more selected from (C) a silicone oil, a nonpolar organic compound, and a low polarity organic compound that are liquid from 5 to 100° C.

The powder in oil dispersion of the present invention can be appropriately prepared according to a known method such as the methods described below.

1. A method in which the powder composition obtained as described above is added to and dispersed in ester oil, a hydrocarbon solvent, or a similar oil agent.
2. A method in which the silicone surfactant is dissolved or dispersed in the oil agent described above, the powder is added thereto, and the mixture is blended using a ball mill, a bead mill, a sand mill, or a similar disperser.

The obtained powder in oil dispersion can be compounded as-is in a preparation for external use (particularly in a cosmetic composition).

The powder composition and the powder in oil dispersion comprising the silicone surfactant according to the present invention can be suitably used as a preparation for external use, particularly for a cosmetic composition or a cosmetic raw material.

(B) Powder or Coloring Agent

The powder or coloring agent (B) used in the powder composition, the powder in oil dispersion, and the like according to the present invention is a component that is commonly used in a cosmetic composition and includes white and colored pigments as well as extender pigments. The white and colored pigments are used to impart color and the like to the cosmetic composition, and the extender pigments are used to improve the tactile sensation and the like of the cosmetic composition. In the present invention, white and colored pigments as well as extender pigments commonly used in cosmetic compositions can be used as the powder without any particular restriction. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range of 1 nm to 100 μm. Particularly, when compounding the powder or coloring agent as a pigment, preferably one or two or more selected from an inorganic pigment powder, an organic pigment powder, and a resin powder having an average diameter in a range of 1 nm to 20 μm is compounded.

Examples of the powder include inorganic powders, organic powders, surfactant metal salt powders (metallic soaps), colored pigments, pearl pigments, metal powder pigments, and the like. Compounded products of these pigments can be used. Furthermore, the surfaces of these pigments may be water-repellent treated.

Specific examples include the same powders or colorants recited in paragraphs 0150 to 0152 of Patent Document 5 (WO2011/049248, filed by the present applicant).

The powders or coloring agents described above are preferably treated using other powder dispersants or surface treatment agents. In particular, the powders or coloring agents may be dispersed or surface-treated by the novel powder treatment agents and treatment methods proposed by the inventors of the invention of the present application in International Patent Publication No. WO2009/022621, Japanese Unexamined Patent Application Publication No. 2011-148784, Japanese Unexamined Patent Application Publication No. 2011-149017, Japanese Unexamined Patent Application Publication No. 2011-246704, Japanese Unexamined Patent Application Publication No. 2011-246705, Japanese Unexamined Patent Application Publication No. 2011-246706, International Patent Publication No. WO2009/022621, International Patent Publication No. WO2011/049246, International Patent Publication No. WO2011/049248, Japanese Patent Application 2011-286973, and the like, or treated to form a slurry using these novel powder treatment agents and the aforementioned oil agents. These novel treatment agents have an excellent improving effect on the unique texture and performance such as dispersion stability, so improving effects on the functionality, texture, storage stability, and the like of the cosmetic can be anticipated when used in combination with the novel cosmetic raw material of the present invention.

Of the powders recited, description of a silicone elastomer powder shall be given. The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the side chain or the molecular terminal and a diorganopolysiloxane having an unsaturated hydrocarbon group such as an alkenyl group or the like on the side chain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. In addition, by carrying out surface treatment using the silicone surfactant, it is possible to impart a moist feeling to touch without reducing the suede-like feeling to touch of a silicone elastomer powder. Furthermore, in cases where the silicone elastomer powder and the silicone surfactant are compounded in a cosmetic composition, dispersion stability of the powder throughout the entire cosmetic composition can be improved and a cosmetic composition that is stable over time can be obtained.

The silicone elastomer powder can be in various forms such as spherical, flat, amorphous, or the like. The silicone elastomer powder may also be in the form of an oil dispersion. With the cosmetic composition of the present invention, the silicone elastomer powder is particulate in form, and the primary particle size observed using an electron microscope and/or the average primary particle size measured by laser analysis or scattering is in a range of 0.1 to 50 μm. Additionally, a silicone elastomer powder having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

Of these silicone elastomer powders, specific examples of silicone elastomer spherical powders are the same as those recited in paragraph 0168 of Patent Document 5 (WO2011/049248, filed by the present applicant), and as recited in paragraphs 0150 to 0152 of the same publication, and may be a silicone elastomer powder that has been subjected to any type of water-repellent treatment.

The mixture of the silicone surfactant (A) and the powder or coloring agent (B) is a form in which the powder is dispersed in the silicone surfactant, and a compounded amount of the powder in the mixture is not particularly limited but is preferably in a range of 50 to 99 wt. % and more preferably in a range of 80 to 90 wt. % of the entire mixture.

(C) Oil Agent

The oil agent used in the powder in oil dispersion and the like according to the present invention preferably is one or more oil agent selected from a silicone oil, a nonpolar organic compound, and a low polarity organic compound that are liquid from 5 to 100° C. A hydrocarbon oil and a fatty acid ester oil are preferable as the nonpolar organic compound and the low polarity organic compound. These oil agents are components that are widely used, particularly as base materials of make-up cosmetic compositions. These oil agents may be combined with one or two or more types of commonly known vegetable oils and fats, animal oils and fats, higher alcohols, liquid triglyceride fatty acids, artificial sebums, or fluorine-based oils. The silicone surfactant also displays superior dispersibility in these non-silicone-based oil agents and, therefore the hydrocarbon oil and the fatty acid ester oil can be stably compounded in a cosmetic composition and moisturizing characteristics imparted by these non-silicone-based oil agents can be maintained. Thus, the silicone surfactant can improve stability over time of these non-silicone-based oil agents in a cosmetic composition. Particularly, compared with conventionally known polyether-modified silicones, the silicone surfactant according to the present invention has prominently superior compatibility with hydrocarbon oils such as isododecane and isohexadecane. Thus, there is a merit in that dispersibility and compounding stability can be further improved (as desired) in not only conventional silicone-based formulations, but also hydrocarbon solvent-based formulations.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition of the present invention. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone-based oil agent (e.g. a hydrocarbon oil, a fatty acid ester oil, or the like), the cosmetic composition comprising a non silicone-based oil agent along with a silicone oil is advantageous in that a smoother, more luxurious tactile sensation is imparted.

These oil agents are the same as those recited in paragraphs 0130 to 0135, paragraph 0206, and the like of Patent Document 5 (WO2011/049248, filed by the present applicant). Examples of the fluorine-based oil include perfluoropolyether, perfluorodecalin, perfluorooctane, and the like.

A compounded amount of the oil agent in the powder in oil dispersion of the present invention is not particularly limited but is preferably in a range of 0.1 to 50 wt. % and more preferably in a range of 0.5 to 25 wt. % in the raw material for use in cosmetic compositions.

The silicone surfactant and the powder composition or the powder in oil dispersion comprising the silicone surfactant can be suitably used as a preparation for external use, particularly for a cosmetic composition or a cosmetic raw material. Such preparations for external use, particularly cosmetic compositions or medicaments are within the scope of the present invention.

Particularly, the silicone surfactant and the powder composition or the powder in oil dispersion comprising the silicone surfactant can be advantageously used as a make-up cosmetic composition raw material. Such make-up cosmetic compositions comprising the silicone surfactant and the powder composition or the powder in oil dispersion comprising the silicone surfactant particularly are within the scope of the preferable embodiments of the present invention.

Water (D) can be further compounded in the cosmetic composition of the present invention and, thereby, the cosmetic composition of the present invention may take the form of an oil-in-water emulsion or a water-in-oil emulsion. In this case, the cosmetic composition of the present invention displays superior emulsion stability and sensation during use. Preparation of a hydrous cosmetic composition and an emulsion cosmetic composition is the same as recited in paragraphs 0128 to 0146 and the like of Patent Document 5 (WO2011/049248, filed by the present applicant).

A uniformly soluble product (emulsion premix) that is the cosmetic raw material is formed by mixing the silicone surfactant with the powder and the oil agent optionally in the presence of ethanol or a similar alcohol. The premix is mixed with water using the device described above. Thus, a cosmetic composition in the form of a uniform oil-in-water emulsion or water-in-oil emulsion can be produced.

The cosmetic composition of the present invention can further comprise (E) other surfactants. These other surfactants are components that function as cleansing components of the skin or the hair or, alternatively, as the oil agent or an emulsifier, and can be selected as desired depending on the type and function of the cosmetic composition. More specifically, the other surfactants can be selected from the group consisting of an anionic surfactant, a cationic surfactant, a nonionic surfactant, an amphoteric surfactant, and a semipolar surfactant. Preferably a silicone-based nonionic surfactant is used in combination.

These surfactants are the same as those recited in paragraphs 0162, 0163, 0195 to 0201, and the like of Patent Document 5 (WO2011/049248, filed by the present applicant). The silicone surfactant used in the present invention has a hydrophilic moiety and a hydrophobic moiety in the molecule and, therefore, has functionality as a dispersing agent. Thus, in cases where used in combination with a silicone-based nonionic surfactant, the component (A) functions as an aid to enhance the stability of the nonionic surfactant and may improve overall stability of the formulation. Particularly, the silicone surfactant is preferably used in combination with polyoxyalkylene-modified silicones, polyglyceryl-modified silicones, glyceryl-modified silicones, and sugar alcohol-modified silicones. Moreover, the silicone-based nonionic surfactants described above in which an alkyl branch, a straight chain silicone branch, a siloxane dendrimer branch, or the like is (as desired) provided with the hydrophilic group can be advantageously used.

Depending on the purpose thereof, the cosmetic composition of the present invention can comprise one or two or more polyhydric alcohols and/or lower monohydric alcohols as a component (F). These alcohols are the same as those recited in paragraphs 0159, 0160, and the like of Patent Document 5 (WO2011/049248, filed by the present applicant).

Depending on the purpose thereof, the cosmetic composition of the present invention can comprise one or two or more inorganic salts and/or organic salts as a component (G). These salts are the same as those recited in paragraph 0161 and the like of Patent Document 5 (WO2011/049248, filed by the present applicant).

Depending on the purpose thereof, the cosmetic composition of the present invention can include at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax as a component (H). These silicone-based components are the same as those recited in paragraphs 0161 to 0193 and the like of Patent Document 5 (WO2011/049248, filed by the present applicant). Examples of the component (H) other than those recited in Patent Document 5 include (H-1): a silicone polyester elastomer gel described in WO2007/109240 and WO2009/006091 in which compatibility with various components is enhanced and stable thickening effects are displayed as a result of introducing a polyoxypropylene group. Examples of commercially available products thereof include Dow Corning EL-8050 ID SILICONE ORGANIC ELASTOMER BLEND, Dow Corning EL-8051 IN SILICONE ORGANIC ELASTOMER BLEND, Dow Corning EL-7040 HYDRO ELASTOMER BLEND; and (H-2): PITUITOUS SILICONE FLUIDS described in WO2011/028765 and WO2011/028770. At least one type selected from these products can be used depending on the purpose of the cosmetic composition of the present invention. Furthermore, the liquid and slightly-crosslinkable organopolysiloxane proposed in Japanese Patent Application No. 2010-289722 and the domestic priority claimed therefrom (filed by the present applicant) can be used in the present invention.

The cosmetic composition of the present invention can, depending on the purpose of the cosmetic composition, comprise one or two or more water-soluble polymers as a component (J). These water-soluble polymers are the same as those recited in paragraph 0201 and the like of Patent Document 5 (WO2011/049248, filed by the present applicant).

The cosmetic composition of the present invention can, depending on the purpose of the composition, comprise one or two or more ultraviolet light blocking components as a component (K). These ultraviolet light blocking components are the same as the organic and inorganic ultraviolet light blocking components recited in paragraphs 0202 to 0204 and the like in Patent Document 5 (WO2011/049248, filed by the present applicant). However, ultraviolet light blocking components that can be particularly preferably used include at least one type selected from the group consisting of microparticle titanium oxide, microparticle zinc oxide, paramethoxy cinnamic acid 2-ethylhexyl, 4-tert-butyl-4'-methoxydibenzoylmethane, diethylamino hydroxybenzoyl hexyl benzoate, benzotriazole-based UV absorber, 2,4,6-tris[4-(2-ethylhexyloxycarbonyl)anilino]1,3,5-triazine (INCI: ethylhexyl triazine), 2,4-bis-6-(4-methoxyphenyl)-1,3,5-triazine (INCI: bis-ethylhexyloxyphenol methoxyphenyl triazine, trade designation: Tinosorb® S), and similar triazine-based UV absorbers. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

In the cosmetic composition of the present invention, by using the raw material for use in cosmetic compositions comprising the silicone surfactant and the ultraviolet light blocking component together, the ultraviolet light blocking component can be stably dispersed in the cosmetic composition and the tactile sensation and the storage stability of the entire cosmetic composition can be improved. Therefore, superior UV blocking capacity can be imparted to the cosmetic composition.

In the cosmetic composition of the present invention, a total compounded amount of the ultraviolet light blocking component with respect to the entire cosmetic composition is preferably in a range of 0.1 to 40.0 wt. % (mass %), and more preferably in a range of 0.5 to 15.0 wt. % (mass %).

Various components other than the components described above can be used in the cosmetic composition of the present invention, provided that such use does not impair the effects of the present invention. Examples thereof include oil-soluble gelling agents, organo-modified clay minerals, preservatives, bioactive components, skin beautifying components, pH adjusting agents, antioxidants, solvents, chelating agents, moisturizing components, perfumes, and the like. These cosmetic product-use optional components are the same as those recited in paragraphs 0207, 0208, 0220 to 0228, and the like of Patent Document 5 (WO2011/049248, filed by the present applicant).

Additionally, in cases where the cosmetic composition according to the present invention is an anti-perspirant, or depending on the purpose of the cosmetic composition, the cosmetic composition can contain an anti-perspiration active component and/or a deodorant agent. These anti-perspirants and deodorant agents are the same as those recited in paragraphs 0209 to 0219 and the like of Patent Document 5 (WO2011/049248, filed by the present applicant). Likewise, in cases where the cosmetic composition according to the present invention is an anti-perspirant composition, the preparation, methods of use, and the like of the various anti-perspirant compositions are the same as those recited in paragraphs 0234 to 0275 and the like of Patent Document 5 (WO2011/049248, filed by the present applicant).

The preparation for external use according to the present invention is not particularly limited, provided that it is a composition for application to the human body as a cosmetic composition or a medicament. Specific examples of cosmetic composition products of the present invention include skin cleansing agent products, skin care products, makeup products, anti-perspirant products, ultraviolet light blocking products, and similar skin use cosmetic products; hair use cleansing agent products, hair dressing products, hair use coloration products, hair growth products, hair rinsing products, hair conditioning products, hair treatment products, and similar hair use cosmetic products; and bath use cosmetic products. Examples of the medicament of the present invention include hair regrowth agents, hair growth promoters, analgesics, germicides, anti-inflammatory agents, refreshing agents, and skin anti-aging agents, but are not limited thereto.

The types, forms, and containers of the preparation for external use according to the present invention are the same as those recited in paragraphs 0230 to 0233 and the like of Patent Document 5 (WO2011/049248, filed by the present applicant), but the silicone surfactant is particularly useful as a raw material for various make-up cosmetic compositions. Additionally, the cosmetic composition according to the present invention is most advantageous as a make-up cosmetic composition comprising the silicone surfactant (A), the powder or colorant (B), and the silicone oil, nonpolar organic compound, or low polarity organic compound (C) that is liquid from 5 to 100° C.

Specific examples of the make-up cosmetic composition include cleansing gels, cleansing creams, cleansing foams, cleansing milks, cleansing lotions, face washing creams, eye makeup removers, face washing foams, liquid soaps (body soaps), hand soaps, gel-like soaps, bar soaps, facial rinses, body rinses, shaving creams, removers, acne treatment cosmetics, and similar skin cleansing agent products; skin creams, scalp treatments, skin milks, milk lotions, emulsions, toners, moisturizing liquids, beautifying liquids, facial packs, body powders, essences, shaving lotions, massage lotions, and similar skin care products; foundations, liquid foundations, oil-based foundations, makeup bases, powders, face powders, lipsticks, lip creams, muddy colored lipsticks or rouges, lip glosses, eye shadows, eye liners, eye creams, eyebrow pencils, eyelash cosmetic products, eyebrow pencils, eyebrow blushes, mascaras, blushers, cheek cosmetics (cheek color, cheek rouge), manicures, pedicures, nail colors, nail laquers, enamel removers, nail polishes, and similar makeup products; deodorants and similar anti-perspirants; and sunscreen agents, tanning use medicaments (sun tanning agent), and similar ultraviolet light blocking products.

EXAMPLES

Hereinafter, the present invention is described in detail with reference to Practical Examples and Comparative Examples, but it should be understood that the present invention is not limited to these Practical Examples. The viscosity (kinetic viscosity) values are measured at 25° C. In the following compositional formulas, Me$_3$SiO groups (or Me$_3$Si group) are notated as "M", Me$_2$SiO groups are notated as "D", and MeHSiO groups are notated as "D$^H$". Units in which a methyl group in D is modified by any substituent is notated as D$^R$.

Practical Example 1

<Synthesis of Co-Modified Organopolysiloxane Compound: Silicone Surfactant P1>

147.0 g of methylhydrogenpolysiloxane represented by the average composition formula MD$_{37}$D$^H_{13}$M, 106.6 g of 1-hexadecene, and 46.4 g of an allyl polyether represented by CH$_2$=CH$_2$CH$_2$O—(C$_2$H$_4$O)$_{10}$—H were added in stages in the presence of 0.07 g of a platinum catalyst in a reaction vessel. The mixture was reacted for several hours at around 65 while agitating under a stream of nitrogen. It was confirmed that the reaction was complete through an alkali decomposition gas generation method (the remaining Si—H groups were decomposed using a KOH ethanol/water solution, and the reaction rate was calculated from the volume of the generated hydrogen gas). Then 150 ppm of NaHSO$_4$ and 1.5 pph of ion-exchanged water were added to the reaction liquid. The mixture was stirred for 30 minutes at around 65° C., followed by stripping to remove water and low-boiling components. The resulting product was subjected to filtration. Thus, 270 g of a co-modified organopolysiloxane represented by the average composition formula MD$_{37}$D$^{R1}_{10.6}$D$^{R2}_{2.4}$M was obtained.

In this formula, R$^1$ and R$^2$ have the structures described below.

$R^1$=—C$_{16}$H$_{33}$ $R^2$=—C$_3$H$_6$O—(C$_2$H$_4$O)$_{10}$—H

Practical Example 2

<Synthesis of Co-Modified Organopolysiloxane Compound: Silicone Surfactant P2>

111.3 g of methylhydrogenpolysiloxane represented by the average composition formula MD$_{38}$D$^H_{12}$M, 55.7 g of 1-dodecene, and 33.0 g of an allyl polyether represented by CH$_2$=CH$_2$CH$_2$O—(O$_2$H$_4$O)$_{10}$—H were added in stages in the presence of 0.05 g of a platinum catalyst in a reaction vessel. The mixture was reacted for several hours at around 65° C. while agitating under a stream of nitrogen. It was confirmed that the reaction was complete through an alkali decomposition gas generation method (the remaining Si—H groups were decomposed using a KOH ethanol/water solution and the reaction rate was calculated from the volume of the generated hydrogen gas). The reaction liquid was heated up to 145° C. under reduced pressure to remove low boiling components. Then the liquid was cooled down to 70° C. and 150 ppm of NaHSO$_4$ and 1.5 pph of ion-exchanged water were added to it. The mixture was stirred for 30 minutes at around 65° C., followed by stripping to remove water and low-boiling components. The resulting product was subjected to filtration. Thus, 180 g of a co-modified organopolysiloxane represented by the average composition formula MD$_{38}$D$^{R3}_{10.0}$D$^{R2}_{2.0}$M was obtained. In this formula, R$^2$ is synonymous with the structure described above and R$^3$ has the structure described below.

$R^3$=—C$_{12}$H$_{25}$

Practical Example 3

<Synthesis of Co-Modified Organopolysiloxane Compound: Silicone Surfactant P3>

93.8 g of methylhydrogenpolysiloxane represented by the average composition formula MD$_{31}$D$^H_{15}$M, 66.3 g of 1-dodecene, and 39.9 g of an allyl polyether represented by CH$_2$=CH$_2$CH$_2$O—(C$_2$H$_4$O)$_{10}$—H were added in stages in the presence of 0.05 g of a platinum catalyst in a reaction vessel. The mixture was reacted for several hours at around 65° C. while agitating under a stream of nitrogen. It was confirmed that the reaction was complete through an alkali decomposition gas generation method (the remaining Si—H groups were decomposed using a KOH ethanol/water solution, and the reaction rate was calculated from the volume of the generated hydrogen gas). Then 150 ppm of NaHSO$_4$ and 1.5 pph of ion-exchanged water were added to the reaction liquid. The mixture was stirred for 30 minutes at around 65° C., followed by stripping to remove water and low-boiling components. The resulting product was subjected to filtration. Thus, 180 g of a co-modified organopolysiloxane represented by the average composition formula MD$_{31}$D$^{R3}_{12.2}$D$^{R2}_{2.8}$M was obtained. R$^2$ and R$^3$ are synonymous with the structures described above.

Practical Example 4

<Synthesis of Co-Modified Organopolysiloxane Compound: Silicone Surfactant P4>

118.2 g of methylhydrogenpolysiloxane represented by the average composition formula MD$_{51.8}$D$^H_{10.2}$M, 55.3 g of 1-hexadecene, and 26.5 g of an allyl polyether represented by CH$_2$=CH$_2$CH$_2$O—(C$_2$H$_4$O)$_{10}$—H were added in stages in the presence of 0.05 g of a platinum catalyst in a reaction vessel. The mixture was reacted for several hours at around 65° C. while agitating under a stream of nitrogen. It was confirmed that the reaction was complete through an alkali decomposition gas generation method (the remaining Si—H groups were decomposed using a KOH ethanol/water solution, and the reaction rate was calculated from the volume of the generated hydrogen gas). Then 150 ppm of NaHSO$_4$ and 1.5 pph of ion-exchanged water were added to the reaction liquid. The mixture was stirred for 30 minutes at around 65° C., followed by stripping to remove water and low-boiling components. The resulting product was subjected to filtration. Thus, 180 g of a co-modified organopolysiloxane represented by the average composition formula MD$_{51.8}$D$^{R1}_{8.2}$D$^{R2}_{2.0}$M was obtained. In this formula, R$^1$ and R$^2$ are synonymous with the structures described above.

<Organopolysiloxane Compound C1>

An organopolysiloxane compound C1 used in the comparative experiments is an organopolysiloxane represented by the average composition formula MD$_{63}$D$^{R1}_{23}$D$^{R4}_5$M, having a number-average molecular weight of about 13,500. This compound C1 can be easily synthesized using methylhydrogenpolysiloxane represented by the average composition formula MD$_{63}$D$^H_{28}$M, 1-hexadecene, and an allyl polyether represented by CH$_2$=CH$_2$CH$_2$O—(C$_2$H$_4$O)$_7$—H as starting materials.

<Organopolysiloxane Compound C2>

An organopolysiloxane compound C2 used in the comparative experiments is an organopolysiloxane represented by the average composition formula MD$_{22}$D$^{R1}_{5.9}$D$^{R2}_{1.0}$M. This compound C2 can be easily synthesized in the same manner as that described for the Practical Examples using methylhydrogenpolysiloxane represented by the average composition formula MD$_{22}$D$^H_{6.9}$M and an allyl polyether represented by CH$_2$=CH$_2$CH$_2$O—(O$_2$H$_4$O)$_{10}$—H as starting materials.

The average composition formulae of the co-modified organopolysiloxane compounds P1 to P4 according to the present invention, and Comparative co-modified organopolysiloxane compounds C1 and C2 according to the comparative examples, which were synthesized according to the methods described above, are shown in Table 1.

TABLE 1

| | Average composition formula | n1 + n2 + n3 | C6-C30Alkyl content [wt %] |
|---|---|---|---|
| Co-modified organopolysiloxanes | | | |
| P1 | $MD_{37}D^{R1}_{10.6}D^{Q2}_{2.4}M$ | 50.0 | 33.1 |
| P2 | $MD_{38}D^{R3}_{10.0}D^{Q2}_{2.0}M$ | 50.0 | 26.5 |
| P3 | $MD_{31}D^{R3}_{12.2}D^{Q2}_{2.8}M$ | 46.0 | 30.3 |
| P4 | $MD_{51.8}D^{R1}_{8.2}D^{Q2}_{2.0}M$ | 62.0 | 24.7 |
| Comparative organopolysiloxanes | | | |
| C1 | $MD_{63}D^{R1}_{23}D^{Q4}_{5}M$ | 91.0 | 38.1 |
| C2 | $MD_{22}D^{R1}_{5.9}D^{Q2}_{1.0}M$ | 28.9 | 33.0 |

In the tables, the structures and types of the functional groups are as follows.

$R^1 = -C_{16}H_{33}$ $Q^2 = -C_3H_6O-(C_2H_4O)_{10}-H$ $R^3 = -C_{12}H_{25}$ $Q^4 = -C_3H_6O-(C_2H_4O)_7-H$

Preparation method for water-in-oil emulsion (E1) composition 1. 11.5 g of dimethylpolysiloxane (6 cs), 11.5 g of mineral oil and 2.0 g of one silicone surfactant selected from the listed organopolysiloxane No. P1-P4, C1-C2 in the table 1 were placed in a 200 mL container.
2. The compound was agitated and the surfactant was uniformly dispersed or dissolved in the oil agent (oil phase A).
3. 0.5 g of Sodium Chloride (salt) and 68.5 g of ion exchanged water were placed in a separate container. The salt was dissolved by mixing using a spatula. Furthermore, 6 g of 1,3-butylene glycol was mixed and dissolved therein (aqueous phase B).
4. The saw teeth of the homo-dispersion were immersed in the oil phase A and, the aqueous phase B was poured into the oil phase A at a constant rate over a period of about 45 seconds, while agitating at 1,000 rpm.
5. The rotational speed of the homo-dispersion was increased to be 3500 rpm, and the contents were homogeneously emulsified by stirring for 2 minutes.
6. Agitation was stopped. Then, the oily component adhered to the inner wall of the container was scraped off using a spatula and mixed with the produced emulsion.
7. The contents were homogeneously emulsified by stirring for 3 minutes with the rotational speed of the homo-disper at 3500 rpm.

The components used in the preparation of each emulsion are as follows.
(1) Dimethylpolysiloxane (6 cs): SH 200 6 cs (Dow Corning Toray)
(2) Mineral oil—HICAL K160 (KANEDA Co., Ltd)
(3) 1,3-Butanediol, Wako Special Grade (Wako Pure Chemical Industries, Ltd.)
(4) Sodium chloride (KANTO CHEMICAL CO., INC.)

The evaluation results are shown in Table 2.

Preparation method for water-in-oil emulsion (E2) composition Except for using 23.0 g of mineral oil instead of 11.5 g of dimethylpolysiloxane (6 cs), 11.5 g of mineral oil, water-in-oil emulsion (E2) composition was prepared in the same Preparation method for water-in-oil emulsion (E1) composition aforementioned. The evaluation results are shown in Table 2.

Evaluation of Dispersion Stability

Slurry-like microparticle dispersions were prepared according to the formulations and preparation methods shown in Preparation of dispersion below. These microparticle dispersions were then evaluated from the standpoints of dispersion characteristics and change in viscosity with time. 1,000 m·Pas was set as the standard for the viscosity of the slurries and those that had viscosities that were lower than 1,000 m·Pas were considered to be "low viscosity" and those that were higher than 1,000 m·Pas were considered to be "high viscosity". The results are shown in Table 2.

The components used in the preparation of each dispersion are as follows.
(1) micro-particle powder: Fine particulate titanium dioxide
   Trade designation: MT-01 (manufactured by Tayca Corporation)
   Particle size: 10 nm
(2) micro-particle powder: Fine particulate zinc oxide
   Trade designation: FINEX-30S-LPT (manufactured by Sakai Chemical Industry Co., Ltd.)
   Particle size: 35 nm
(3) Dispersing medium: isohexadecane
   Trade designation: ISOHEXADECANE (manufactured by Lanxess)

Example

Preparation of Dispersion (Zinc Oxide)

Each slurry-like zinc oxide dispersion was produced by mixing 18 g of the fine particulate zinc oxide, 1.5 g of one silicone surfactant selected from the listed organopolysiloxanes No. P1-P4, C1-C2, and 10.5 g of a isohexadecane; adding 120 g of zirconia beads (ϕ0.8 mm) thereto; and mixing the mixture using a paint shaker (PAINT SHAKER, manufactured by Asada Iron Works Co., Ltd.) for 15 hours. After removing the zirconia beads, viscosity of the obtained zinc oxide slurry was measured. The slurries were kept in 35 mL glass bottles. The bottles were capped and allowed to sit at rest in a 50° C. constant temperature bath to check stability. A series of Zinc oxide slurry using said silicone surfactants were evaluated by following evaluation standards.

○○: Low viscosity slurry producible, no increase in viscosity with time
○Δ: Low viscosity slurry producible, slowly increase in viscosity with time
○x: Low viscosity slurry producible, rapid increase in viscosity with time
ΔΔ: High viscosity slurry producible, no increase in viscosity with time
Δx: High viscosity slurry producible, rapid increase in viscosity with time Example: Preparation of Dispersion (Titanium Dioxide)

Each slurry-like titanium dioxide dispersion was produced by mixing 12 g of the fine particulate titanium dioxide, 3 g of one silicone surfactant selected from the listed organopolysiloxanes No. P1-P4, C1-C2, and 15 g of isohexadecane; adding 120 g of zirconia beads (ϕ0.8 mm) thereto; and mixing the mixture using a paint shaker for 15 hours. After removing the zirconia beads, viscosity of the obtained zinc oxide slurry was measured.

TABLE 2

|  |  | Practical Examples | | | | Comparative Examples | |
|---|---|---|---|---|---|---|---|
|  |  | P1 | P2 | P3 | P4 | C1 | C2 |
| Emulsion stability | Viscosity of E1 | ○ | ○ | ○ | ○ | Δ | ○ |
|  | Emulsion Particles of E1 | ○ | ○ | ○ | ○ | ○ | ○ |
|  | Viscosity of E2 | ○ | ○ | ○ | ○ | Δ | ○ |
|  | Emulsion Particles of E2 | ○ | ○ | ○ | ○ | ○ | ○ |
| Viscosity of Zinc oxide slurry | | ○○ | ΔX | ○Δ | ○X | ΔΔ | ○X |
| Viscosity of Titanium dioxide slurry [mmPa·s] | | 287 | 577 | 257 | 275 | 1110 | 115 |

Evaluation of Viscosity Stability 25 g of each water-in-oil emulsion composition was measured into a 35 mL glass bottle. The bottles were capped and allowed to sit at rest in a 50° C. constant temperature bath for one month. 25000 mPa·s was set as the standard for the viscosity of the emulsions and those that had viscosities that were lower than 25000 mPa·s were considered to be "low viscosity" and those that were higher than 25000 mPa·s were considered to be "high viscosity".
The viscosity of the emulsions before and after sitting was evaluated according to the following standards.
○: Low viscosity with variation=<±25% and appearance was uniform without change
Δ: High viscosity with variation=<±25% and appearance was uniform without change
Measurement of Emulsified Particle Size
Observations and photographs using an optical microscope (at a magnification of 1000 times) were taken on the day after the water-in-oil emulsion compositions were prepared and the weight average particle diameter was calculated using image analysis software.
The emulsified particle size was evaluated according to the following standards.
○: Weight average particle diameter smaller than 4 μm.
Δ: Weight average particle diameter larger than 4 μm As shown in Table 2, with the novel silicone surfactants P1 to P4 according to the present invention, stable and low viscosity emulsions and low viscosity powder in oil dispersions (slurries) with titanium dioxide were producible. Especially, P1 and P3 that have more than 30 wt % of alkyl content in their organopolysiloxane structures could make low viscosity powder in oil dispersions (slurries) with zinc oxide without rapid increase of viscosity. In contrast, with the comparative compound C1, it was hard to make both low viscosity emulsions and low viscosity slurries. Though C2 could make low viscosity emulsions and slurries, the viscosity of zinc oxide slurry increase rapidly despite having more than 30 wt % of C6-C30 alkyl content. As shown in Table 2, furthermore, the novel silicone surfactants P1 to P4 according to the present invention also performed both function of emulsifying oils and of dispersing inorganic powders without any treatment (ex. Acid treatment) of the co-modified organopolysiloxane itself.
These results show that performance varies greatly depending on how structure is controlled, even when the same polyether-modified silicone is used. That is, with the silicone surfactant of the present invention, it is thought that its specific molecular range can provide both emulsification and dispersant capabilities. If the molecule is smaller than the present invention, it becomes hard to control dispersibility. In contrast, if the molecule is larger than the present invention, it becomes hard to make both low viscosity emulsions and low viscosity slurries.

Formulation Examples

Hereinafter, examples are given based on specific formulations for the cosmetic composition of the present invention, but it is understood that the types and formulations of the cosmetic composition of the present invention are not limited to the types and formulations described in these examples. Furthermore, although said co-modified organopolysiloxane "P1" is applied in all of following formulation examples, the organopolysiloxane "P1" can be replaced with the same parts of other co-modified organopolysiloxane of this invention (including co-modified organopolysiloxane "P2" to "P4" or mixture thereof) to design the preferred formulation. Skilled person in the art also can add other cosmetic additives (ex. known preservatives or pH adjusting agent etc.) to this formulations.
Formulation Example 1: Water in Oil foundation 1
Formulation Example 2: Oil in Water foundation 1
Formulation Example 3: Water in Oil foundation 2
Formulation Example 4: Oil in water foundation 2
Formulation Example 5: Water in oil cream
Formulation Example 6: Water in oil lotion
Formulation Example 7: Oil in water lotion
Formulation Example 8: Gel
Formulation Example 9: Toner
Formulation Example 10: Oil in wax stick
Formulation Example 11: Clear gel
Formulation Example 12: Anhydrous gel
Formulation Example 13: Antiperspirant gels
Formulation Example 14: Loose powder
Formulation Example 15: Lip Gloss
Formulation Example 16: Lipstick
Formulation Example 17: Mascara
Formulation Example 18: Cleaner
Formulation Example 19: Shampoo
Formulation Example 20: Leave in conditioner
Formulation Example 21: Rinse off conditioner
Formulation Example 22: Ointment Formulation Example 1: Water in Oil Foundation 1

Components

| Ingredient | Wt. % |
|---|---|
| Phase A | |
| P1 | 1.5 |
| Caprylyl Methicone | 2 |
| Dimethicone | 13 |
| Ethylhexyl Methoxycinnamate | 3 |
| C30-45 Alkyl Methicone | 2 |
| Cyclopentasiloxane (and) Polypropylsilsesquioxane | 1 |
| Mica | 0.5 |
| Silica Silylate | 0.4 |
| Phase B | |
| Titanium dioxide | 4 |
| Talc | 2 |
| Zinc Oxide | 1 |
| Iron Oxides Yellow | 0.65 |

-continued

| Ingredient | Wt. % |
|---|---|
| Iron Oxides Red | 0.05 |
| Iron Oxide Black | 0.1 |
| Caprylyl Methicone | 2 |
| P1 | 1.5 |
| Phase C | |
| Sodium Chloride | 1 |
| Glycerin | 8 |
| Algae extract | 1 |
| Deionized Water | 54.2 |
| Dimethicone/Vinyl Dimethicone Crosspolymer (and) Silica (and) Butylene Glycol | 0.5 |
| Phase D | |
| Phenoxyethanol (and) Ethylhexylglycerin | 0.5 |
| Phase E | |
| Frangance | 0.1 |

Procedure:
Heat and keep temperature of phase A to melt wax well;
Mix phase B well;
Mix phase A and Phase B well;
Mix phase C well;
Drop phase C into Phase (A and B) slowly;
Add residue ingredients and mix all ingredients well.

Formulation Example 2: Oil in Water Foundation 1

Components

| Ingredient | Wt. % |
|---|---|
| Phase A | |
| Glyceryl Stearate/PEG-100 Stearate (PEG = polyethylene glycol) | 2 |
| Coconut Alcohol/Coco-Glucoside | 2 |
| Stearyl Dimethicone | 2 |
| P1 | 0.3 |
| Phase B | |
| Butyl Methoxydibenzoylmethane | 1.5 |
| Benzophenone-3 | 1 |
| Ethylhexyl Salicylate | 5 |
| Octocrylene | 5 |
| Phase C | |
| Premix of Pigments | 5 |
| Trimethylsiloxysilicate (and) Polypropylsilsesquioxane | 1.5 |
| Isododecan | 1.5 |
| Dimethicone/Dimethicone Crosspolymer | 4 |
| Tocopheryl Acetate | 0.5 |
| Caprylyl Methicone | 3 |
| Phase D | |
| Water | 31.7 |
| 3-o-ethyl ascorbic acid | 0.5 |
| Disodium EDTA (EDTA = Ethylene Diamine Tetraacetic Acid) | 0.1 |
| Sodium polyacrylate (and) dimethicone (and) cyclopentasiloxane (and) trideceth-6 (and) PEG/PPG-18/18 dimethicone (PPG = polypropylene glycol) | 2 |
| Phase E | |
| Glycerin | 5 |
| Water | 26 |
| Potassium Cetyl Phosphate | 0.2 |

-continued

| Ingredient | Wt. % |
|---|---|
| Phase F | |
| Benzyl Alcohol (and) Methylchloroisothiazolinone (and) Methylisothiazolinone | 0.1 |
| Phase G | |
| Fragrance | 0.1 |
| Premix of Pigments | |
| Titanium dioxide | 36.0 |
| Iron oxide yellow | 2.5 |
| Iron oxide red | 1.0 |
| Iron oxide black | 0.5 |
| P1 | 10.0 |
| Phenyltrimethicone | 50.0 |

Procedure:
Make premix of pigments by grinding them by three rolls grinder;
Hear to melt all ingredients in phase A and mix all;
Mix phase A, phase B and phase C with premix of pigments well;
Heat phase E and mix until get homogenous gel;
Mix phase D and E well;
Add phase (D and E) into Phase (A, B, and C) and mix well;
Homogenous all ingredients together until get uniform products.

Formulation Example 3: Water in Oil Foundation 2

Components

| Ingredient | Wt. % |
|---|---|
| Phase A | |
| P1 | 1 |
| Isododecane | 2 |
| Cyclopentasiloxane | 5 |
| Phenyltrimethicone | 2 |
| C12-15 alkyl benzoate | 4 |
| Ethylhexyl Methoxycinnamate | 7.5 |
| Trimethylsiloxy silicate (and) Polypropylsilsesquioxane | 2 |
| Dimethicone/vinyldimethicone crosspolymer (and) Silica | 2 |
| Phase B | |
| P1 | 1 |
| Caprylyl Methicone | 2 |
| Titanium dioxide | 5.1 |
| Yellow iron oxide | 0.3 |
| Red iron oxide | 0.05 |
| Black iron oxide | 0.03 |
| Phase C | |
| Water | 57.52 |
| Sodium Chloride | 2 |
| glycerin | 3 |
| Propylene Glycol | 3 |
| Phenoxyethanol (and) Methylparaben (and) Ethylparaben (and) Propylparaben (and) Butylparaben | 0.5 |

Procedure:
To mix all ingredients in phase A together;
To mix all ingredients in phase B together;
To mix all ingredients in phase C together;
Mix phase A and B together;
Add phase C to phase (A and B) under speed mixing until getting homogenous product.

Formulation Example 4: Oil in Water Foundation 2

Components

| Ingredient | Wt. % |
|---|---|
| Phase A | |
| P1 | 0.3 |
| PEG-12 Dimethicone | 2 |
| Diisostearyl Malate | 5 |
| Cyclopentasiloxane (and) Dimethicone Crosspolymer | 5 |
| Isohexane | 5 |
| Dimethicone/Vinyl Dimethicone Crosspolymer (and) Silica (and) Butylene Glycol | 1 |
| Titanium Dioxide (CI 77891)(and) Hydrogenated Coco-Glycerides(and) Iron Oxide yellow Pigment yellow 11) (and) Red Iron Oxide (Pigment red 101) (and) Black Iron Oxide (Pigment black 11) (and) Ethylcellulose (and) PVA | 3 |
| Phase B | |
| Water | 68 |
| Licorice extract | 0.2 |
| Glycerin | 8 |
| Butylene Glycol | 2 |
| Phase C | |
| Phenoxyethanol (and) Ethylhexylglycerin | 0.5 |

Procedure:
To mix all ingredients in phase A together;
To mix all ingredients in phase B together;
Mix phase A and B together under high speed mixing;
Add phase C to phase (A and B) under speed mixing until getting homogenous product.

Formulation Example 5: Water in Oil Cream

Components

| Ingredient | Wt. % |
|---|---|
| Phase A | |
| P1 | 1.5 |
| Diethylhexyl Carbonate | 8 |
| Caprylic/Capric Triglyceride | 8 |
| Ethylhexyl Palmitate | 8 |
| Microcrystalline Wax | 0.5 |
| Castor Oil | 0.5 |
| Phase B | |
| Water | 68.5 |
| Sodium Chloride | 2 |
| Glycerin | 3 |

Procedure:
To mix all ingredients in phase A together;
To mix all ingredients in phase B together;
Add phase B to phase A slowly under high speed mixing until getting homogenous product.

Formulation Example 6: Water in Oil Lotion

Components

| Ingredient | Wt. % |
|---|---|
| Phase A | |
| Cyclopentasiloxane (and) Dimethiconol (and) Dimethicone | 4 |
| Cyclopentasiloxane | 7 |
| Ethylhexyl Methoxycinnamate | 5 |
| Ethylhexyl Salicylate | 4 |
| P1 | 4 |
| Sorbitan Trioleate | 0.5 |
| Phase B | |
| Titanium Dioxide (and) Alumina (and) Stearic Acid | 3.3 |
| Zinc Oxide (and) Trimethoxycaprylylsilane | 1.3 |
| Phenyl Trimethicone | 5.4 |
| Phase C | |
| Water | 43.5 |
| Glycerin | 10 |
| Propylene Glycol | 10 |
| Sodium Chloride | 1.5 |
| DMDM Hydantoin (and) Iodopropynyl Butylcarbamate | 0.3 |
| Perfume | 0.2 |

Procedure:
Mix phase A well.
Mix phase B well
Mix A and B well.
Mix phase C well.
Slowly add phase C to phase (A + B), drop by drop while mixing at 700 rpm.

Formulation Example 7: Oil in Water Lotion

Components

| Ingredient | Wt. % |
|---|---|
| Phase A | |
| PEG-100 stearate | 1.5 |
| P1 | 0.2 |
| Cyclohexasiloxane (and) Cyclopentasiloxane | 3 |
| squalane | 2 |
| Caprylyl dimethicone | 2 |
| Mineral oil | 2 |
| Jojoba oil | 2 |
| Phase B | |
| Acrylates/C10-30 Alkyl Acrylate Crosspolymer | 0.2 |
| Glycerin | 10 |
| Water | 66.6 |
| Propylene Glycol | 10 |
| DMDM Hydantoin (and) Iodopropynyl Butylcarbamate | 0.3 |

Procedure:
Heat phase A and mix well;
Mix phase B well and heat to 70 centigrade degree;
Add phase A to phase B under mixing;
Homogenize for a while to get a uniform product.

Formulation Example 8: Gel

Components

| Ingredient | Wt. % |
|---|---|
| Phase A | |
| Acrylates/C10-30 Alkyl Acrylate Crosspolymer | 0.2 |
| water | 29 |

| Ingredient | Wt. % |
|---|---|
| phase B | |
| P1 | 2 |
| Cyclopentasiloxane | 2 |
| Ethylhexyl Methoxycinnamate | 4 |
| Ethylhexyl Salicylate | 2 |
| Phase C | |
| water | 50 |
| glycerin | 10 |
| Phase D | |
| Triethylamine | 0.3 |
| Phase E | |
| Phenoxyethanol (and) Ethylhexylglycerin | 0.5 |

Procedure:
Make dispersion of phase A;
Mix phase B well;
Mix phase C well;
Mix phase A, B and C together,.
Add phase D and keep mixing;
Add residue ingredients and mix well

Formulation Example 9: Toner

Components

| Ingredient | Wt. % |
|---|---|
| Phase A | |
| P1 | 1 |
| Caprylic/capric Triglyceride | 1 |
| Dimethicone | 0.3 |
| Phenyltrimethicone | 0.3 |
| Phase B | |
| Tween ® 20 (=Polyoxyethylene (20) sorbitan monolaurate) | 1 |
| Ethanol | 5 |
| Glycerin | 5 |
| Bis-PEG-18 Methyl Ether Dimethyl Silane | 0.3 |
| licorice extract | 0.1 |
| Water | 86 |

Procedure:
Heat phase A and mix well;
Mix phase B well and heat to 70 centigrade degree;
Add phase A to phase B under mixing;
Homogenize for a while to get a uniform product.

Formulation Example 10: Oil in Wax Stick

Components

| Ingredient | Wt. % |
|---|---|
| Phase A | |
| P1 | 2 |
| Cyclopentasiloxane | 8 |
| Stearyl Dimethicone | 1 |
| C30-45 Alkyl Methicone (and) C30-45 Olefin | 9 |
| Shea butter | 0.3 |
| Mineral Oil | 6 |
| Octyl Methoxycinnamate | 4 |
| Butyl Methoxydibenzoylmethane | 1.5 |
| Phase B | |
| Sodium Chloride | 1 |
| Distilled Water | 59.7 |
| Bis-PEG-18 Methyl Ether Dimethyl Silane | 3 |

| Ingredient | Wt. % |
|---|---|
| Water (and) Glycerin (and) Beta-Glucan | 1.2 |
| Propylene Glycol | 3 |
| Phase C | |
| Perfume and preservative | 0.3 |

Procedure:
Heat and mix phase A well;
Heat and mix phase B well;
Add phase B to phase A slowly under high speed mixing;
Add phase C to above mixture and mix well;
Pour on mold to get final product.

Formulation Example 11: Clear Gel

Components

| Ingredient | Wt. % |
|---|---|
| Phase A | |
| Glycerin | 43.0 |
| Water | 27.0 |
| Phase B | |
| P1 | 5.0 |
| Isododecane | 10.0 |
| Myristyl laurate | 5.0 |
| Caprylyl Methicone (and) PEG-12 Dimethicone/PPG-20 Crosspolymer | 10.0 |

Procedure:
Mix phase A well;
Mix phase B well;
Measure refraction index of phase A and B separated;
Adjust phase A to match its refraction index with phase B
Add Phase A to Phase B slowly and mix well.

Formulation Example 12: Anhydrous Gel

Components

| Ingredient | Wt. % |
|---|---|
| Phase A | |
| P1 | 4.0 |
| Caprylic/Capric Triglyceride | 5.0 |
| Dimethicone (and) Dimethicone crosspolymer | 15.0 |
| Phase B | |
| L-ascorbic acid | 10.0 |
| Glycerin | 66.0 |

Procedure:
Mix phase A well;
Heat glycerin to high temperature and add L-ascorbic acid into it under mixing until getting clear solution;
Drop phase B into Phase A slowly;
Mix final gel well.

Formulation Example 13: Antiperspirant Gels

Components

| Ingredient | Wt. % |
|---|---|
| Phase A | |
| P1 | 5.0 |
| Caprylyl Methicone (and) PEG-12 Dimethicone/PPG-20 Crosspolymer | 5.0 |
| Cyclopentasiloxane | 19.5 |

-continued

| Ingredient | Wt. % |
|---|---|
| Phase B | |
| Algae extract | 0.5 |
| Aluminum chloride | 25.0 |
| propylene glycol | 7.0 |
| Water | 38.0 |

Procedure:

Mix phase A well;

Dissolve aluminum chloride in mixture of water and propylene glycol under mixing;

Drop phase B into Phase A slowly;

Mix final gel well.

Formulation Example 14: Loose Powder

Components

| Ingredient | Wt. % |
|---|---|
| Phase A | |
| Talc | 68.0 |
| Titanium dioxide | 12.0 |
| Pigment (CI 15850, triethoxycaprylysilane; CI 42090 & Triethoxycaprylylsilane; Iron oxides (and) hydrogenated lecithin) | 3.0 |
| HDI/Trimethylol Hexyllactone Crosspolymer (And) Silica | 5.0 |
| Dimethicone/Vinyldimethicone Crosspolymer (and) Silica | 1.0 |
| Mica | 1.5 |
| Pigment (CI 77891 & CI 77491 & Mica & Triethoxycaprylylsilane) | 1.0 |
| P1 | 5.5 |
| Dimethicone | 3.0 |

Procedure:

Add ingredient one by one to the pigment mixer;

Mix all ingredients well.

Formulation Example 15: Lip Gloss

Components

| Ingredient | Wt. % |
|---|---|
| Phase A | |
| Dimethicone | 15.0 |
| Cyclopentasiloxane (and) Dimethiconol | 40.0 |
| Phenyltrimethicone | 10.0 |
| Bis-hydroxyethoxypropyl Dimethicone | 15.0 |
| Dimethicone (and) Trimethylsiloxysilicate | 8.0 |
| Olive oil | 2.0 |
| Ethylhexyl Salicylate | 6.0 |
| P1 | 3.0 |
| Phase B | |
| Silica silylate | 1.0 |

Procedure:

Add ingredient in phase A one by one in order under mixing;

Mix phase A well 75° c.;

Add phase B into phase A under mixing;

Mix phase (A + B) well.

Formulation Example 16: Lipstick

Components

| Ingredient | Wt. % |
|---|---|
| Phase A | |
| Ozocerite | 7.0 |
| Carnauba wax | 12.0 |
| Petrolatum | 5.0 |
| Bee wax | 5.0 |
| Lanolin | 3.0 |
| Candelilla wax | 2.0 |
| Microcrystalline Wax | 2.0 |
| *Euphorbia* Cerifera & Isopropyl Palmitate & Ozokerite & Cetearyl Ethylhexanoate & Isostearyl Alcohol & *Copernicia* Cerifera & Myrystyl Lactate & Synthetic Beeswax & BHT (BHT = butylated hydroxytoluene) | 14.0 |
| C30-45 Alkyldimethylsilyl polypropylsilsesquioxane | 5.0 |
| P1 | 4.0 |
| Phase B | |
| Hydrogenated dimer Dilinoleyl/Dimethylcarbonate Copolymer | 14.0 |
| Oleyl Alcohol | 8.0 |
| Caprylyl Methicone | 9.0 |
| Pigment (Iron Oxide, CI331700, CI 77891, CI 73360, Titanium Dioxide) | 10.0 |

Procedure:

Using pigment mixer mix all pigments well;

Melt all ingredients in phase A and mix well;

Mix phase B well;

Add phase B to phase A and mix well;

Pour phase (A + B) into lipstick mold;

Put mold to refrigerator and keep for 15 minutes;

Take lipstick out of mold and package it.

Formulation Example 17: Mascara

Components

| Ingredient | Wt. % |
|---|---|
| Phase A | |
| Beeswax | 10 |
| Stearyl Dimethicone | 7 |
| *Copernicia* Cerifera (Carnauba) Wax | 3 |
| P1 | 5 |
| Phase B | |
| Pigment (CI 77499 (and) Triethoxycaprylylsilane) | 5 |
| Nylon fiber | 5 |
| Polypropylsilsesquioxane (and) Isododecane | 5.5 |
| Isododecane | 12.5 |
| Phase C | |
| Water | 42 |
| Propylene Glycol | 5 |
| DMDM Hydantoin (and) Iodopropynyl Butylcarbamate | 0.3 |

Procedure:

Heat and mix phase A well;

Mix phase B well;

Heat and mix phase C well;

Add phase C to Phase A with high speed mixing;

Add phase B to mixture of phase A and B under mixing until getting homogenous products.

Formulation Example 18: Cleanser

Components

| Ingredient | Wt. % |
|---|---|
| Phase A | |
| Hydroxy Ethyl Cellulose | 0.4 |
| Water | 31.3 |
| Phase B | |
| Stearic acid | 1.6 |
| Myristic acid | 4.0 |
| Palmitic acid | 3.2 |
| Sodium Laureth Sulfate (and) Glycol Distearate (and) Cocamide MEA (and) Laureth-10 | 2.4 |
| P1 | 4.0 |
| Phase C | |
| Water | 39.6 |
| potassium hydroxide | 6.0 |
| Phase D | |
| Sodium Laureth Sulfate (and) Glycol Distearate (and) Cocamide MEA (MEA = monoethanolamine) (and) Laureth-10 | 4.0 |
| Propylene glycol | 1.6 |
| Glycerin | 1.6 |
| Phase E | |
| Citric acid | 0.2 |
| Propylene Glycol (and) Diazolidinyl Urea (and) Methylparaben (and) Propylparaben | 0.4 |

Procedure:
Heat water to 80° C.;
Disperse hydro ethyl cellulose into water slowly under mixing;
Mix Phase B and keep temperature of Phase B at 80° C.;
Add Phase A to Phase B;
Dissolve potassium hydroxide into water and heat solution to 80° C.;
Add Phase B into Phase C under mixing and keep temperature at 80° C.;
Add Phase D into Phase (A + B + C) and keep mixing until temperature down to 45° C.;
Add Phase E into Phase (A + B + C + D).

Formulation Example 19: Shampoo

Components

| Ingredient | Wt. % |
|---|---|
| Phase A | |
| Sodium Laureth Sulfate (28%) | 32.8 |
| Cocamide Diethanolamine | 5.9 |
| PEG-150 Pentaerythrityl Tetrastearate (and) PEG-6 Caprylic/Capric Glycerides (and) Water | 5.9 |
| Cocamidopropyl Betaine (30%) | 6.6 |
| Octodecyl Trimethyl Ammonium Chloride | 0.3 |
| Lauryl Glucoside | 4.7 |
| P1 | 4.7 |
| Phase B | |
| Water | 39.3 |
| Phase C | |
| DMDM Hydantoin | 0.2 |

Procedure:
Heat phase A to 65° C. and mix it well;
Heat phase B to 45° C.;
Add phase B into Phase A under mixing;
Cool Phase (A + B) to 45° C. in room temperature;
Add phase C into phase (A + B) and mix well.

Formulation Example 20: Leave in Conditioner

Components

| Ingredient | Wt. % |
|---|---|
| Phase A | |
| P1 | 0.5 |
| Sodium Polyacrylate (and) Dimethicone (and) Cyclopentasiloxane (and) Trideceth-6 (and) PEG/PPG-18/18 Dimethicone | 2 |
| Polysorbate 60 | 1 |
| Phenyl Trimethicone | 5 |
| Stearyl Dimethicone | 2 |
| Dimethicone (and) Dimethiconol | 10 |
| Phase B | |
| Water | 66.2 |
| EDTA.2Na | 0.1 |
| Vitamin E | 0.3 |
| D-Panthenol | 0.3 |
| Propylene Glycol | 2 |
| preservative | 0.3 |
| Phase C | |
| Dimethicone/Vinyldimethicone Crosspolymer, Isoceteth-25, Isoceteth-10 | 10 |
| Phase D | |
| Perfume | 0.3 |

Procedure:
Mix phase A well;
Mix phase B well;
Mix phase A and B well;
Add residue to above mixture and mix all well

Formulation Example 21: Rinse Off Conditioner

Components

| Ingredient | Wt. % |
|---|---|
| Phase A | |
| Hydro Ethyl Cellulose | 1.5 |
| Water | 95 |
| Phase B | |
| Octodecyl Trimethyl Ammonium Chloride | 0.3 |
| Cetearyl alcohol | 1.0 |
| P1 | 2 |
| Phase C | |
| DMDM Hydantoin | 0.2 |

Procedure:
Heat water to 80° C.
Disperse hydro ethyl cellulose into water slowly under mixing;
Keep temperature at 80° C.;
Add phase B into Phase A under mixing;
Add Phase C when temperature down to 45° C. and mix well.

Formulation Example 22: Ointment

Components

| Ingredient | Wt. % |
|---|---|
| P1 | 10 |
| Calamine | 10 |
| Talc | 15 |
| Zinc Oxide | 15 |

-continued

| Ingredient | Wt. % |
|---|---|
| Titanium dioxide | 10 |
| Iron Oxides Yellow | 3.5 |
| Iron Oxides Red | 1 |
| Iron Oxide Black | 0.5 |
| Dimethicone | 35 |

Procedure:
Mix all ingredients together by a blender

Specifically, the practical examples and so on in the above-mentioned Patent Document 5 describe emulsions, lip glosses, oil-based foundations, water-in-oil emulsion transparent anti-perspirant compositions, and non-aqueous stick-form anti-perspirant compositions as compositions able to be replaced by the silicone surfactants according to the present invention, and paragraphs [0459] to [0501] also describe the following formulation examples.
Example 1: Emulsion foundation
Example 2: Liquid foundation
Example 3: Foundation
Example 4: Water-in-oil cream
Example 5: Water-in-oil emulsion composition
Example 6: Water-in-oil emulsion rouge (liquid)
Example 7: Liquid rouge
Example 8: Rouge
Example 9: Sunscreen emulsion
Example 10: Emulsion
Example 11: UV blocking cream
Example 12: UV blocking water-in-oil emulsion
Example 13: Sunscreen agent
Example 14: Water-in-oil emulsion sunscreen
Example 15: O/W cream
Example 16: Eye shadow
Example 17: Mascara
Example 18: Mascara
Example 19: Solid powder eye shadow
Example 20: Pressed powder cosmetic
Example 21: Powder foundation
Example 22: Pressed foundation
Example 23: Cream
Example 24: Foundation
Example 25: Water-in-oil emulsion-type sunscreen
Example 26: Lipstick
Example 27: Rouge
Example 28: Foundation
Example 29: Anti-perspirant aerosolized cosmetic composition
Example 30: Nonaqueous pressurized anti-perspirant product
Example 31: Aerosol type anti-perspirant composition
Example 32: Anti-perspirant lotion composition
Example 33: W/O emulsion-type skin preparation for external use
Example 34: Nonaqueous anti-perspirant deodorant stick composition
Example 35: W/O solid anti-perspirant stick composition
Example 36: W/O emulsion type anti-perspirant cream composition
Example 37: Mascara
Example 38: Aftershave cream
Example 39: Solid foundation
Example 40: Daytime use skin-lightening cream
Example 41: Sun tanning cream
Example 42: Polyol/O-type nonaqueous emulsion skin preparation for external use
Example 43: Polyol/O-type nonaqueous emulsion skin preparation for external use

INDUSTRIAL APPLICABILITY

The silicone surfactant according to the present invention has comparatively low molecular weight and superior surface treating properties, and, therefore, can be used in external use preparations, and particularly for industrial applications other than cosmetic compositions. Examples thereof include varnishes and paint additives having excellent heat resistance, weathering resistance, and electrical characteristics; polyol base compounds, foam stabilizers, and modification agents of various types of urethanes and foamed materials; demolding agents and separating agents; antifoam agents; grease and oil compounds; oils used as insulation, polishing agents, water-proofing agents, heating mediums, cooling mediums, lubricants, or the like; modification agents, surface treatment agents, and additives used for rubbers and resins; blending materials, modification agents, and precursors used for silane coupling agents; coating materials and sealing materials used for construction and lining applications; protective agents, lubricants, and buffer agents used for optical fibers and electrical lines; or the like. However, the novel organopolysiloxane copolymer according to the present invention is not limited to such applications.

The invention claimed is:

1. A silicone surfactant comprising a co-modified organopolysiloxane represented by the following general formula (1):

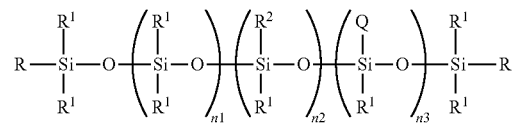

wherein
R$^1$ is a monovalent hydrocarbon group having from 1 to 30 carbons, or is a hydrogen atom;
R$^2$ is a straight or branched monovalent hydrocarbon group having from 6 to 30 carbons;
Q is a hydrophilic group consisting of a polyoxyalkylene group represented by structural formula (2):

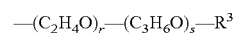

wherein
R$^3$ is a hydrogen atom or an alkyl group having from 1 to 4 carbons,
r is a number in a range of 0 to 100,
s is a number in a range of 0 to 50, and
r+s is a number in a range of 3 to 100;
R is a group selected from R$^1$, R$^2$, and Q;
provided that, when n3=0, at least one R is Q;
(n1+n2+n3) is a number in a range of 40 to 75;
n1 is a number in a range of 1 to 65;
n2 is a number in a range of 1 to 20; and
n3 is a number in a range of 0 to 5.

2. The silicone surfactant of claim 1, wherein the co-modified organopolysiloxane is represented by the following general formula (1-1):

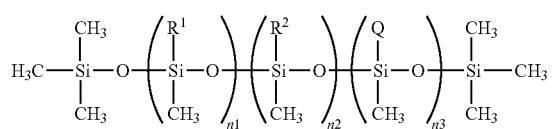

wherein n1 is a number in a range of 2 to 55, n2 is a number in a range of 3 to 20, and n3 is a number in a range of 0.5 to 5.

3. The silicone surfactant of claim 2, having more than 30 wt % of content of hydrocarbon group of $R^2$ having from 6 to 30 carbons, which is calculated by the weight ratio of $R^2$ to the total molecular weight of the co-modified organopolysiloxane.

4. The silicone surfactant of claim 1, having more than 30 wt % of content of hydrocarbon group of $R^2$ having from 6 to 30 carbons, which is calculated by the weight ratio of $R^2$ to the total molecular weight of the co-modified organopolysiloxane.

5. An ingredient comprising the silicone surfactant according to claim 1, wherein the ingredient is selected from the group consisting of an emulsifier, a surface treatment agent, a powder treatment agent, and a dispersant in a cosmetic composition or a medicament.

6. A water-in-oil (W/O) emulsion composition comprising:
(A) the silicone surfactant according to claim 1;
(B) water; and
(C) at least one oil agent.

7. A cosmetic composition or a medicament comprising the W/O emulsion composition according to claim 6.

8. A method of adjusting transparency of the W/O emulsion composition according to claim 6, said method comprising the steps of:
(i) independently mixing an aqueous phase including component (B) and an oil phase including component (A) and component (C);
(ii) adjusting a difference between refractive indexes at 25° C. of both phases so as to be less than or equal to 0.0020 units; and
(iii) emulsifying the aqueous phase into the oil phase.

9. A powder composition comprising:
(A) the silicone surfactant according to claim 1; and
(D) a powder or coloring agent.

10. The powder composition according to claim 9, wherein component (D) is one or two or more selected from the group consisting of an inorganic pigment powder, an organic pigment powder, and a resin powder, having an average diameter in a range of 1 nm to 20 µm.

11. The powder composition according to claim 10, further comprising (C) at least one oil agent.

12. The powder composition according to claim 9, further comprising (C) at least one oil agent.

13. A cosmetic composition or a medicament comprising the powder composition according to claim 9.

14. A preparation for external use comprising the silicone surfactant according to claim 1.

15. The preparation for external use according to claim 14, further defined as a cosmetic composition or a medicament.

16. A cosmetic composition or a medicament comprising the silicone surfactant according to claim 1, wherein the cosmetic composition or the medicament is in a substantially water-free form.

* * * * *